United States Patent
Lindley et al.

(10) Patent No.: US 9,757,505 B2
(45) Date of Patent: Sep. 12, 2017

(54) PRESSURE OUTPUT DEVICE FOR EXTRACORPOREAL HEMODIALYSIS MACHINE

(71) Applicant: Fresenius Medical Care Holdings, Inc., Waltham, MA (US)

(72) Inventors: DeLoy Lindley, Ogden, UT (US); Jose Antonio Badillo, West Haven, UT (US); Michael Parry Smith, Ogden, UT (US); Richard Allen Lasher, Farmington, UT (US); Troy Calvin Dayton, Syracuse, UT (US); Lynn E. Jensen, Syracuse, UT (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

(21) Appl. No.: 14/810,526

(22) Filed: Jul. 28, 2015

(65) Prior Publication Data
US 2016/0089484 A1    Mar. 31, 2016

Related U.S. Application Data

(60) Provisional application No. 62/056,122, filed on Sep. 26, 2014.

(51) Int. Cl.
*G01L 7/00* (2006.01)
*A61M 1/36* (2006.01)
(Continued)

(52) U.S. Cl.
CPC ........ *A61M 1/3639* (2013.01); *A61M 1/3641* (2014.02); *A61M 39/227* (2013.01);
(Continued)

(58) Field of Classification Search
CPC ..... A61M 1/3639; A61M 1/3641; G01L 7/00; G01L 13/025
(Continued)

(56) References Cited

U.S. PATENT DOCUMENTS

| 4,666,598 A | * | 5/1987 | Heath ................. A61M 1/3621 210/137 |
| 5,554,113 A | * | 9/1996 | Novak ............... A61B 5/02154 604/30 |

(Continued)

FOREIGN PATENT DOCUMENTS

| DE | 102012016395 A1 | 2/2013 |
| EP | 0330891 A1 | 9/1989 |

(Continued)

OTHER PUBLICATIONS

Gambro, Pressure sensing device and use of the same in a connecting structure, Nov. 20, 2008, WO 2008/140395.*

(Continued)

*Primary Examiner* — Michael A Lyons
*Assistant Examiner* — Nigel Plumb
(74) *Attorney, Agent, or Firm* — Kilyk & Bowersox, P.L.L.C.

(57) ABSTRACT

A pressure output device (POD) assembly for sensing fluid pressure in a fluid processing system, is provided. This POD assembly includes a shell defining a shell interior, and a movable diaphragm disposed in the shell interior and separating the shell interior into a flow-through chamber and a pressure sensing side. A sensor port is in fluid communication with the pressure sensing side. An inlet port and an outlet port are in fluid communication with the flow-through chamber. The inlet port and the outlet port define an inlet and an outlet, respectively, of a flow-through channel that passes through the flow-through chamber. A boss protrudes from
(Continued)

the interior wall of the shell and extends into the flow-through channel to prevent occlusion of flow under different pressure conditions within the flow-through chamber.

27 Claims, 15 Drawing Sheets

(51) Int. Cl.
    *A61M 39/22*     (2006.01)
    *G01L 7/08*     (2006.01)
    *G01L 19/00*     (2006.01)
    *G01L 19/06*     (2006.01)

(52) U.S. Cl.
    CPC ............... *G01L 7/08* (2013.01); *G01L 7/082* (2013.01); *G01L 19/0023* (2013.01); *G01L 19/0618* (2013.01); *A61M 2205/12* (2013.01); *A61M 2205/3331* (2013.01)

(58) Field of Classification Search
    USPC ........................................ 73/715, 700, 716
    See application file for complete search history.

(56) References Cited

U.S. PATENT DOCUMENTS

| | | | | |
|---|---|---|---|---|
| 5,641,911 | A * | 6/1997 | Ryhanen | G01L 11/008 73/715 |
| 5,693,008 | A * | 12/1997 | Brugger | A61M 1/3641 600/485 |
| 5,720,598 | A * | 2/1998 | de Chizzelle | F04B 51/00 417/53 |
| 6,014,800 | A * | 1/2000 | Lee | G01L 9/0072 29/25.41 |
| 6,016,705 | A * | 1/2000 | Baur | G01L 9/0051 73/719 |
| 6,526,357 | B1 * | 2/2003 | Soussan | A61M 1/3496 702/100 |
| 7,013,223 | B1 * | 3/2006 | Zhang | F02M 65/003 417/53 |
| 7,487,681 | B1 * | 2/2009 | Allen | G01L 9/0042 73/715 |
| 7,566,205 | B2 * | 7/2009 | Kinugawa | F04B 43/067 417/244 |
| 8,092,414 | B2 * | 1/2012 | Schnell | A61M 1/3639 210/741 |
| 8,197,231 | B2 * | 6/2012 | Orr | F04B 7/02 137/512.4 |
| 8,210,049 | B2 * | 7/2012 | Brugger | A61M 1/3626 600/485 |
| 8,273,049 | B2 * | 9/2012 | Demers | A61M 1/1037 417/477.2 |
| 8,292,594 | B2 * | 10/2012 | Tracey | A61M 1/1037 417/395 |
| 8,323,194 | B2 * | 12/2012 | Robinson | A61B 5/14503 600/309 |
| 8,357,298 | B2 * | 1/2013 | Demers | 210/321.6 |
| 8,429,979 | B2 * | 4/2013 | Kuwahara | G01L 9/0072 361/283.4 |
| 8,617,070 | B2 * | 12/2013 | Imran | A61B 1/00082 600/309 |
| 2008/0216898 | A1 * | 9/2008 | Grant | A61M 1/1037 137/154 |
| 2010/0186518 | A1 * | 7/2010 | Jonsson | A61M 1/3641 73/756 |
| 2012/0271226 | A1 * | 10/2012 | Farrell | A61M 1/28 604/29 |
| 2013/0042692 | A1 * | 2/2013 | Fini | A61M 1/3639 73/706 |
| 2013/0115105 | A1 | 5/2013 | Tracey et al. | |
| 2014/0199193 | A1 * | 7/2014 | Wilt | A61M 1/1037 417/477.2 |
| 2015/0306299 | A1 * | 10/2015 | Stuva | A61M 1/3639 604/121 |
| 2015/0314058 | A1 | 11/2015 | O'Mahony | |

FOREIGN PATENT DOCUMENTS

| | | |
|---|---|---|
| EP | 2383004 A1 | 11/2011 |
| WO | 2008140395 A1 | 11/2008 |
| WO | 2009127683 A1 | 10/2009 |

OTHER PUBLICATIONS

International Search Report and Written Opinion issued in corresponding International Patent Application No. PCT/US2015/042333 dated Oct. 15, 2015 (13 pages).
Cobe Centrysystem 3 Dialysis Control Unit (Operator's Manual), Sep. 1988, COBE Laboratories, Inc., Lakewood, CO (see p. 4-33 A-V Pressure Not Changing Alarm).

\* cited by examiner

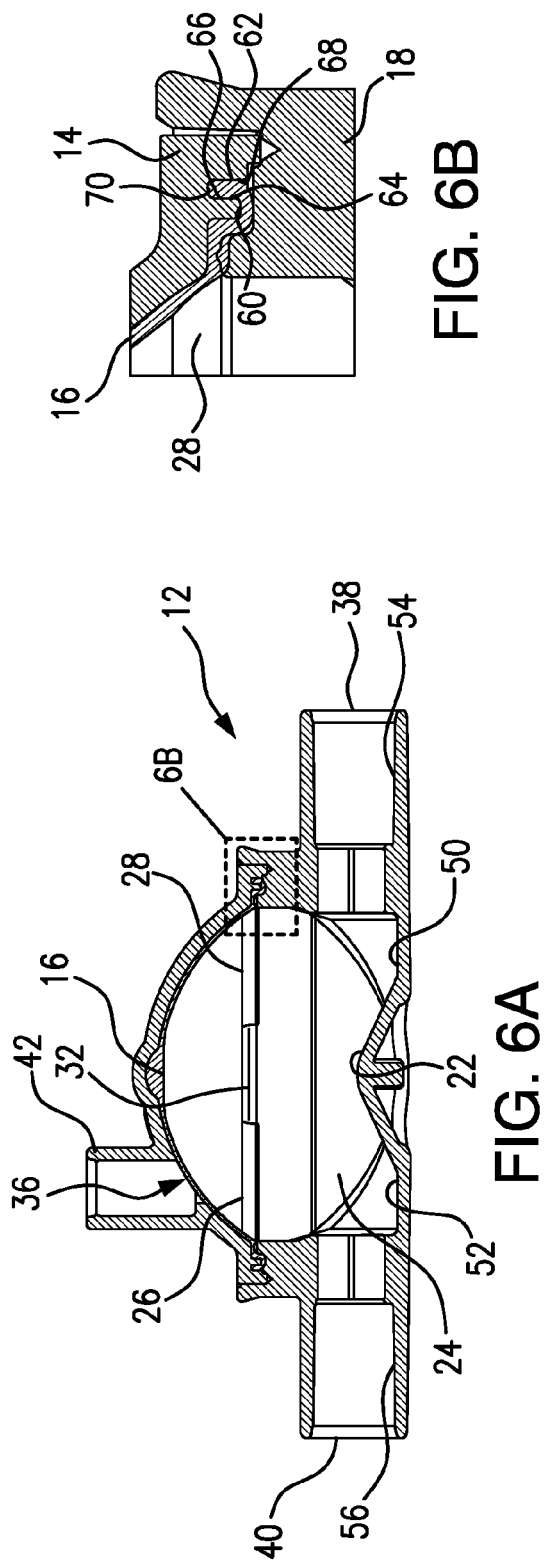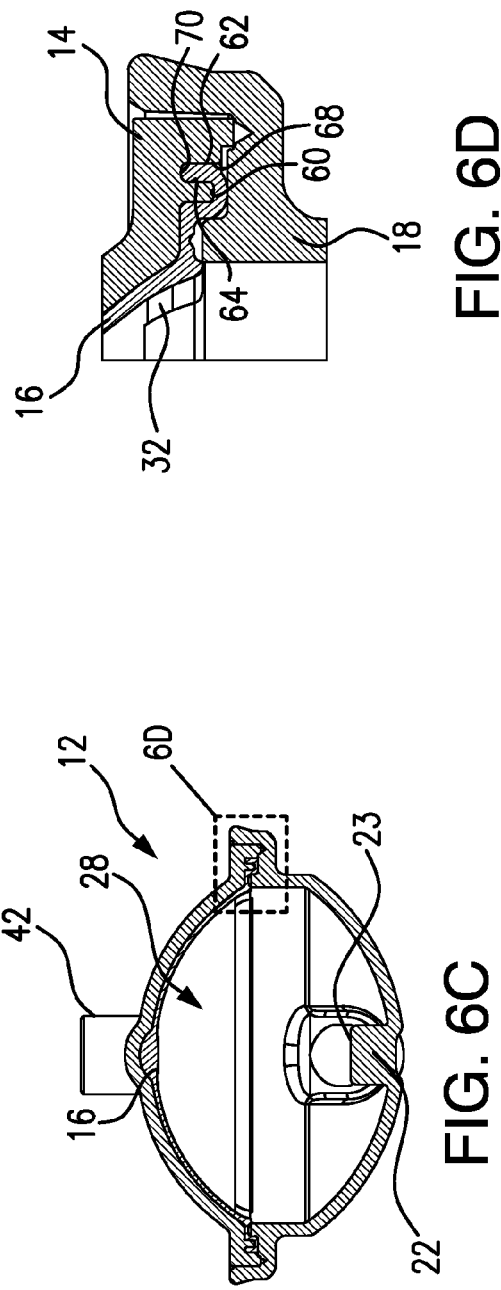

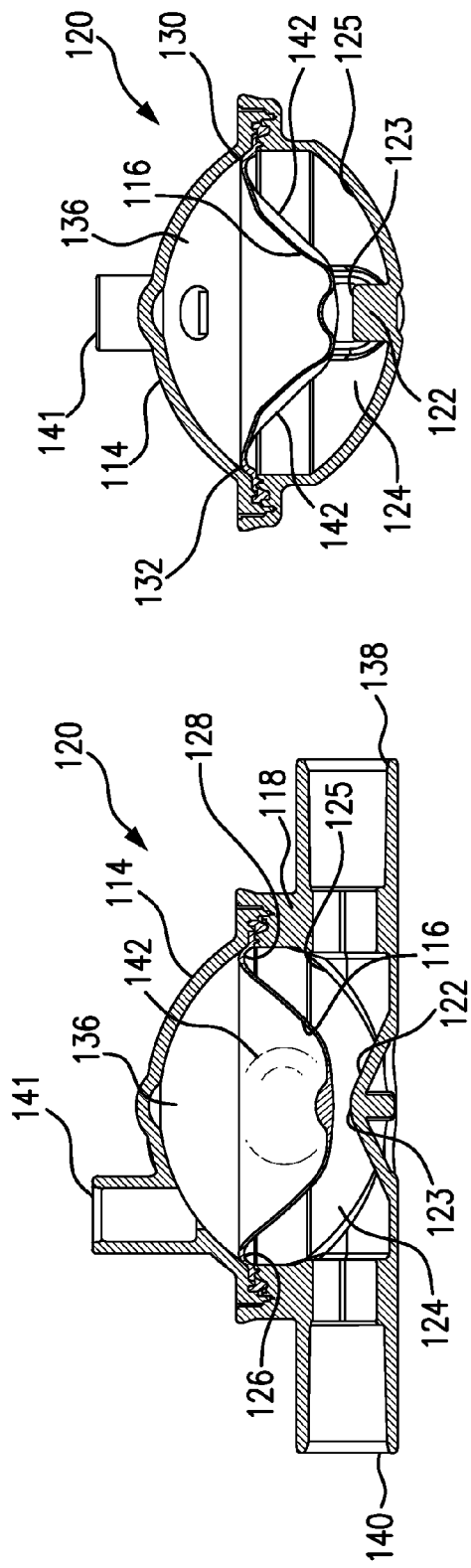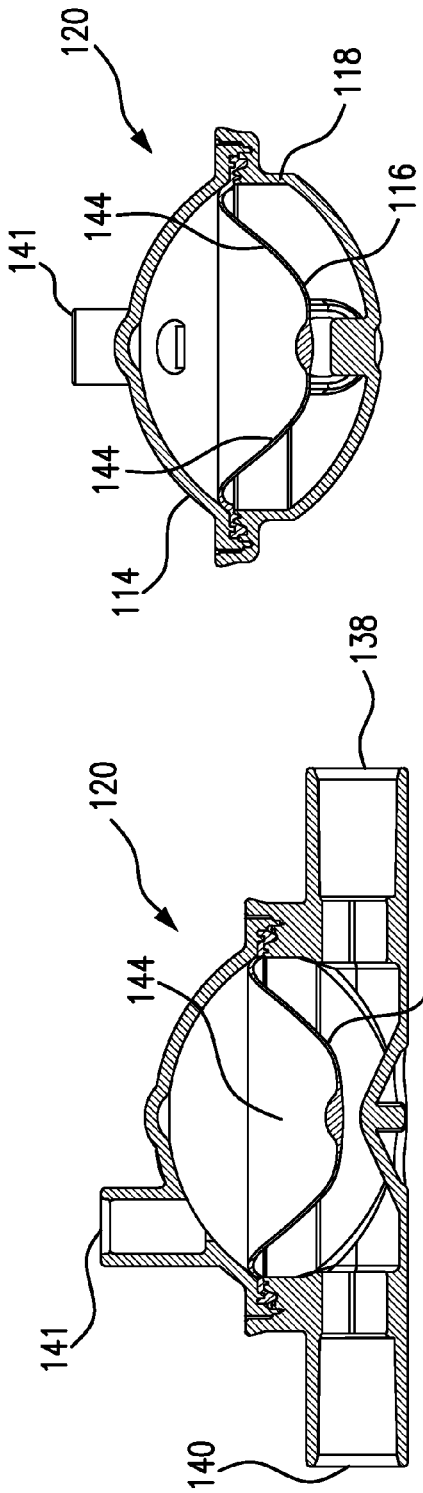

PRESSURE OUTPUT DEVICE FOR EXTRACORPOREAL HEMODIALYSIS MACHINE

This application claims the benefit under 35 U.S.C. §119 (e) of prior U.S. Provisional Patent Application No. 62/056,122, filed Sep. 26, 2014, which is incorporated in its entirety by reference herein.

FIELD OF THE INVENTION

The present invention relates to pressure output devices for measuring fluid pressure in an extracorporeal hemodialysis machine.

BACKGROUND OF THE INVENTION

Hemodialysis machines commonly monitor pressure in an extracorporeal blood circuit, for example, pressure from a blood chamber containing a blood-air interface. An air-filled tube connects the blood chamber to a pressure port of the machine. A transducer protector, containing a hydrophobic membrane, is positioned between the blood chamber and the pressure port. The membrane provides a sterile barrier to the blood circuit and prevents blood contamination of the machine, yet allows air pressure to pass through the membrane and act on the pressure transducer inside the machine. Problems with such a blood-air interface system include clotting, heparin dosage concerns, contamination, and inaccurate pressure measurements. Air contact with blood results in clotting that can collect in portions of the blood circuit, reducing treatment effectiveness. Clotting can also occasionally require replacement of the dialyzer during treatment. To reduce clotting during dialysis, a patient is typically administered a dosage of heparin, sufficient to allow adequate treatment time, yet allow the patient's clotting factor to return to normal levels prior to termination of the treatment. The use of heparin adds cost to the treatment and increases the potential for hazardous blood loss. The hydrophobic membrane in the transducer protector is very thin, and occasionally allows blood contamination of the pressure monitoring circuit on the dialysis machine. When this occurs, the contaminated portion of the machine must be cleaned and sanitized before the machine can be used again. Occasionally, during dialysis, abrupt pressure changes in the blood circuit, or air leaks in the pressure port connection, allow the blood level to reach the hydrophobic membrane in the transducer protector. Blood contact with the membrane occludes air channels through the membrane, which can inhibit or prevent pressure transfer to the transducer of the dialysis machine. This condition can reduce the response time of the machine, to pressure changes, or can prevent pressure monitoring completely.

SUMMARY OF THE INVENTION

According to one or more embodiments of the present invention, a liquid processing circuit including a pressure output device, is provided. The circuit can be an extracorporeal hemodialysis circuit including a pressure measuring device, which facilitates many functions. The pressure measuring device can communicate blood circuit pressure to the pressure port of an extracorporeal blood processing machine, for example, to a hemodialysis machine, without exposing the blood circuit to air. The device can minimize the potential for hazardous restriction of blood flow through the blood side of the device, during pressure-related fault conditions. The device can accurately communicate arterial pressure, for example, in the range of from 0 to −300 mmHg, at elevations of up to 8000 feet. The device can accurately communicate venous pressure, for example, in the range of from 0 to 500 mmHg, at elevations of up to 8000 feet. The device can prevent blood contamination of the pressure monitoring circuit on a hemodialysis machine. In addition, the device can prevent contamination of the blood circuit.

The pressure output device (POD) assemblies of the present invention can be placed along and used in the arterial and venous lines of an extracorporeal circuit, for example, of a dialysis machine, to be used during hemodialysis. The POD assembly provides an airless system for transferring extracorporeal circuit pressures to pressure monitoring ports of the extracorporeal circuit, for example, to the ports of a hemodialysis machine. Each POD assembly has two chambers that are separated from one another by an elastomeric diaphragm. Each chamber can be translucent. Blood can flow through one of the chambers, referred to herein as the flow-through side or chamber of the POD assembly. A volume of air can be contained in the second chamber. As blood flows through the flow-through side of the POD assembly, positive or negative circuit pressure displaces the diaphragm. The respective displacement of the diaphragm compresses or expands the volume of air between the diaphragm and the pressure transducer in the hemodialysis machine, with which the volume of air is in fluid communication. As the air volume changes, the resulting pressure will be detected by the pressure transducer. The POD assembly also protects the pressure transducer from blood contact, and provides a sterile barrier at the interface to the blood circuit. Using the POD assembly of the present invention eliminates the need for a typical transducer protector, including the need for a hydrophobic membrane. The present invention thus also eliminates the problems mentioned above that are associated with the use of a typical transducer protector.

The flow-through side of the POD assembly has two ports, an inlet port and an outlet port. Each port can be solvent-bonded to flexible tubing, such as polyvinylchloride (PVC) tubing, in an extracorporeal circuit. The tubing ports facilitate blood flow through the flow-through side or chamber of the device. The flow-through side also has an internal diamond-shaped boss feature that prevents the diaphragm from occluding blood flow that could potentially cause hemolysis during pressure-related fault conditions.

The second chamber in the POD assembly is referred to herein as the pressure sensing side of the POD assembly. The pressure sensing side has a single port, also referred to as a sensor port, that can be solvent-bonded to flexible tubing. The flexible tubing can attach, via a luer fitting, to a pressure monitoring port of a hemodialysis machine. Both chambers in the POD assembly can be designed with internal volumes to facilitate accurate output of arterial pressures, for example, within a range of from 0 to −300 mmHg, and venous pressures of from 0 to 500 mmHg, even at elevations of up to 8000 feet above sea level. Other designs or volumes can be used to achieve any suitable and/or desired range of pressure sensing, whether for sensing arterial pressure, venous pressure, or any other kind of fluid pressure. Atmospheric pressure and chamber volumes can be directly related to the operating range for pressure output, and in extreme conditions, such as altitudes in excess of 8000 feet, customized or tailored chamber volumes can be used.

BRIEF DESCRIPTION OF THE DRAWINGS

The present invention can be even more fully understood with the reference to the accompanying drawings which are intended to illustrate, not limit, the invention.

FIG. 6A is a cross-sectional side view of an arterial POD assembly according to one or more embodiments of the present invention and showing the POD assembly diaphragm position at the start of a treatment.

FIG. 6B is an enlarged view of section 6B shown in FIG. 6A, illustrating details of the hinge of the diaphragm, and showing the engagement of the POD assembly components with one another.

FIG. 6C is a cross-sectional end view of the arterial POD assembly shown in FIG. 6A.

FIG. 6D is an enlarged view of section 6D shown in 6A illustrating details of one of the two hinge interruptions in the POD assembly diaphragm.

FIG. 7A is a cross-sectional side view of a venous POD assembly according to one or more embodiments of the present invention and showing the POD assembly diaphragm at a treatment start position and the bulge in the diaphragm caused by the diaphragm hinge and hinge interruptions.

FIG. 7B is a cross-sectional end view of the venous POD assembly shown in FIG. 7A.

FIG. 8A is a cross-sectional side view of the venous POD assembly shown in FIGS. 7A and 7B, but at pressures near 0 mmHg, and showing that the bulge appearing in FIGS. 7A and 7B has been displaced.

FIG. 8B is a cross-sectional end view of the venous POD assembly shown in FIG. 8A.

DETAILED DESCRIPTION OF THE INVENTION

Figure 1A:
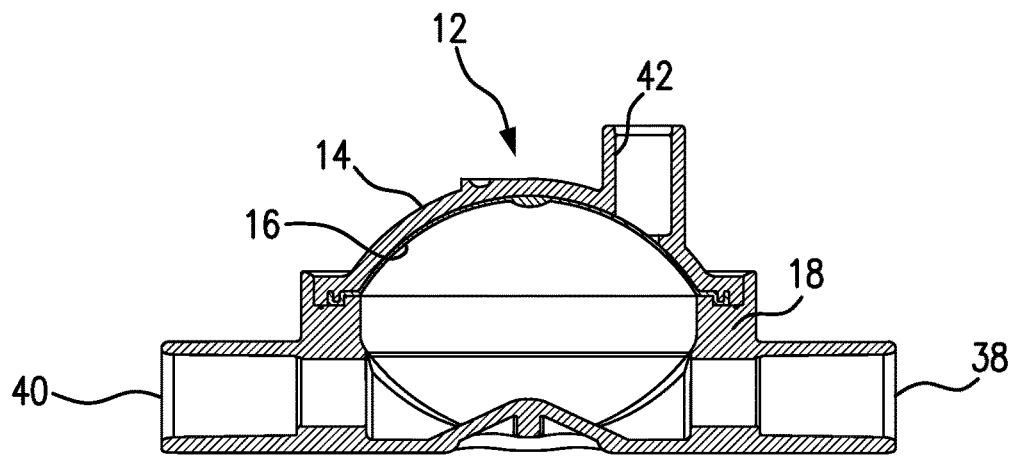
FIG. 1A is a cross-sectional side view taken through the middle of a pressure output device (POD) according to one or more embodiments of the present invention, showing the POD assembly configured for measuring arterial blood circuit pressure and the POD assembly diaphragm positioned at 0 mmHg.
Figure 1B:
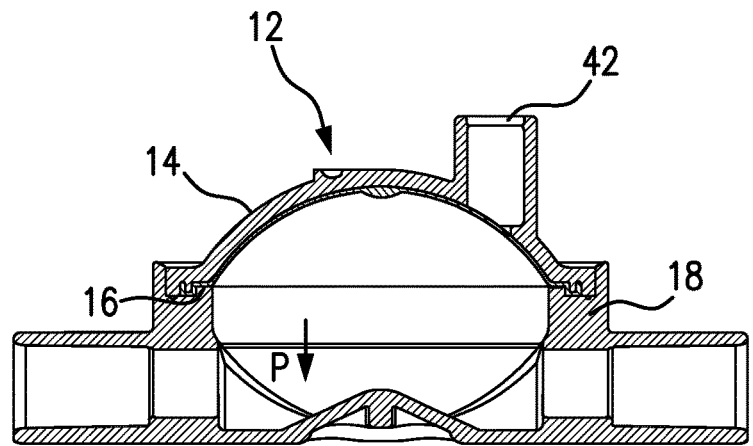
FIG. 1B is a cross-sectional side view of the POD assembly shown in FIG. 1A and indicating the directional movement of the diaphragm as pressure decreases in the arterial blood circuit.
Figure 1C:
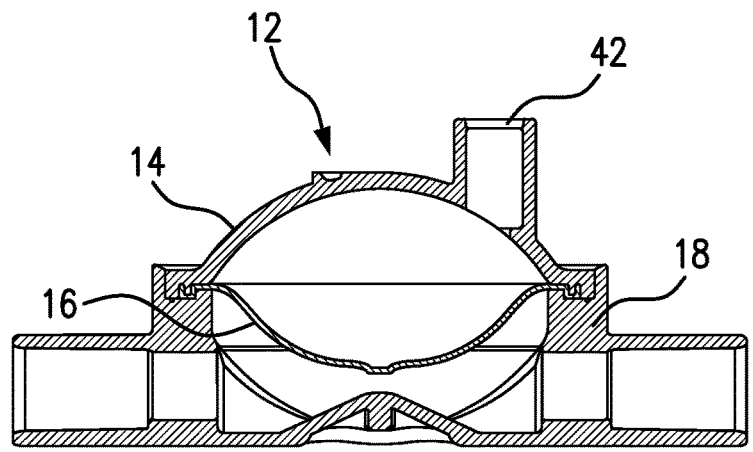
FIG. 1C is cross-sectional side view of the POD assembly shown in FIGS. 1A and 1B but wherein the diaphragm is positioned at the most negative accurately measurable arterial pressure, i.e., at sub-atmospheric pressure of −300 mmHg.

FIGS. 1A-1C are cross-sectional side views of an assembled pressure output device (POD) according to one or more embodiments of the present invention and arranged to measure blood pressure in an arterial circuit. POD assembly 12 is constructed of a cap 14, a diaphragm 16, and a base 18, assembled together. Blood tubing can be connected, for example, by solvent-bonding, to an inlet port 38 and an outlet port 40 on the flow-through side or chamber of the POD assembly. A sensor port 42 is provided in cap 14 and tubing can be connected, for example, by solvent-bonding, to form a communication between sensor port 42 and a pressure sensor port of a hemodialysis machine. For the purpose of simplification, the respective tubings are not shown in FIGS. 1A-2C.

FIG. 1A shows diaphragm 16 in an initial, start position for an arterial circuit. POD assembly 12 is arranged to measure negative pressures, i.e., sub-atmospheric pressures. Diaphragm 16 in FIG. 1A is shown as positioned at zero mmHg. As pressure in the flow-through chamber of POD assembly 12 begins to decrease, diaphragm 16 moves towards the flow-through chamber in the direction shown by arrow P, as shown in FIG. 1B.

FIG. 1C shows diaphragm 16 in a position where it can accurately output the most negative arterial pressure, for example, at −300 mmHg. With diaphragm 16 in the position shown in FIG. 1C, the pressure-sensing side of the POD assembly exhibits a maximum volume for accurate measurement and the POD assembly exerts a negative pressure through sensor port 42, which is communicated to a pressure transducer in the hemodialysis machine. More details of the flow-through chamber, the pressure-sensing side, and the arterial POD assembly in general, are provided in connection with the description of FIGS. 4A-6D below.

Figure 2A:
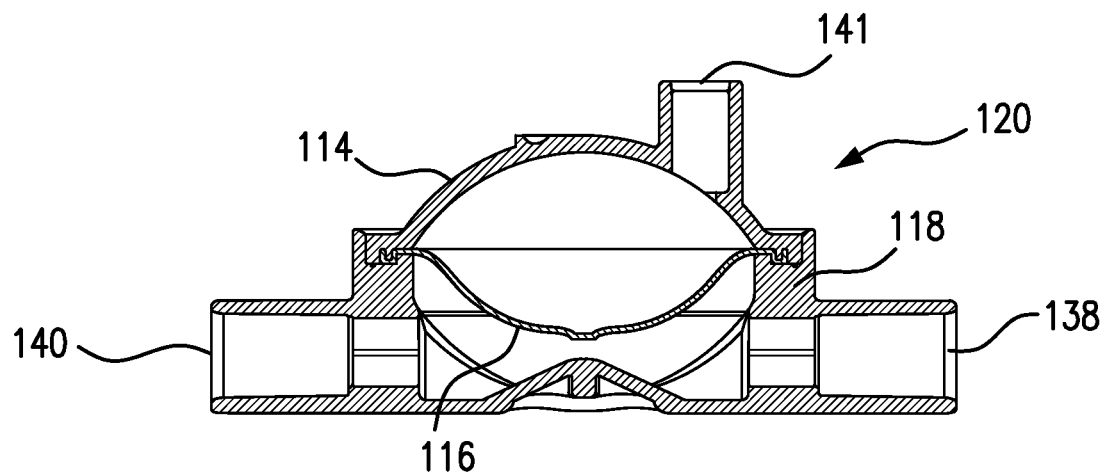
FIG. 2A is a cross-sectional side view taken through the middle of a pressure output device (POD) according to one or more embodiments of the present invention, wherein the POD assembly is configured to measure positive pressure in a venous circuit and the POD assembly diaphragm is positioned at 0 mmHg.
Figure 2B:
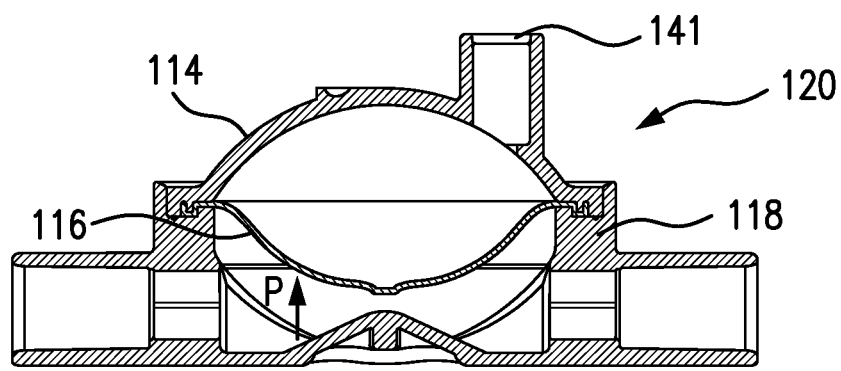
FIG. 2B is cross-sectional side view of the POD assembly shown in FIG. 2A and indicating the directional movement of the POD assembly diaphragm as pressure increases in the venous blood circuit.
Figure 2C:
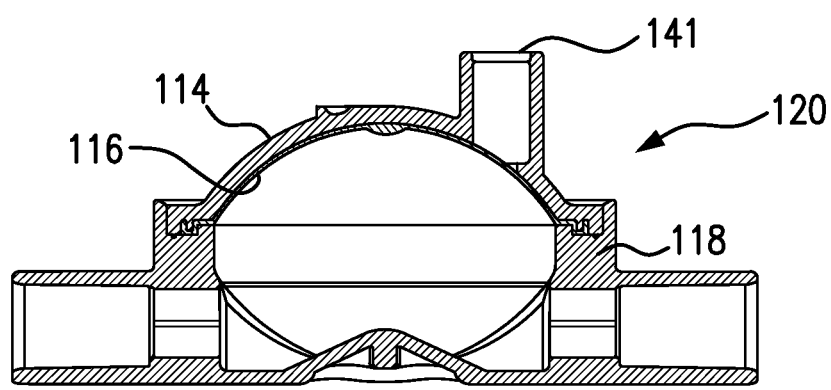
FIG. 2C is a cross-sectional side view of the POD assembly shown in FIGS. 2A and 2B but wherein the diaphragm is in a position that results from exertion of maximum venous pressure.

FIGS. 2A-2C are side cross-sectional views of a POD assembly according to one or more embodiments of the present invention, and arranged to measure blood pressure in a venous circuit, that is, arranged to measure positive blood pressures. FIG. 2A shows a venous POD assembly 120 constructed of a cap 114, a diaphragm 116, and a base 118, assembled together. While different number reference numerals are used to label the components of POD assembly 120, relative to the reference numerals used to label the components of POD assembly 12 shown in FIGS. 1A-1C, it is to be understood that the exact same components can be used for either an arterial POD assembly or a venous POD assembly, and only the initial position of the diaphragm can differ between the two configurations. Accordingly, a set of two POD assemblies can be provided, and, by proper positioning of the diaphragm, either POD assembly can be configured and used to measure arterial pressure and either POD assembly can be configured and used to measure venous pressure. A set of two POD assemblies can be provided wherein the diaphragms have already been positioned to be in the initial or start positions for an arterial POD assembly and for a venous POD assembly, respectively.

Base 118 of POD assembly 120 comprises an inlet port 138 and an outlet port 140 to a flow-through chamber of the POD assembly. Cap 114 can comprise a sensor port 141 on the pressure-sensing side of the POD assembly. More details about the flow-through chamber, the pressure-sensing side, and the venous POD assembly in general, are provided below in connection with the descriptions of FIGS. 7A-10B.

FIG. 2A shows diaphragm 116 in an initial, start position, at zero mmHg, and configured to measure venous pressure. As pressure increases in the blood circuit, resulting from the flow of blood through the flow-through chamber of POD assembly 120, diaphragm 116 moves toward cap 114 in the direction shown by arrow P in FIG. 2B. The movement of diaphragm 116 toward cap 114 compresses air in the pressure-sensing side of POD assembly 120, which thereby increases the pressure of gas in the fluid communication from the pressure-sensing side, through sensor port 141, and to a venous pressure transducer in a hemodialysis machine. FIG. 2C shows diaphragm 116 pushing against and flush with the inner surface of cap 114 at a maximum accurately measurable venous pressure. Adjustments can be made to the amount of air in the pressure-sensing side of POD assembly 120 to avoid having diaphragm 116 reach the extreme position shown in FIG. 2C. Injecting air or gas into the pressure-sensing side, or into a fluid communication communicating with the pressure sensing side, can be used to position diaphragm 116.

Figure 3:
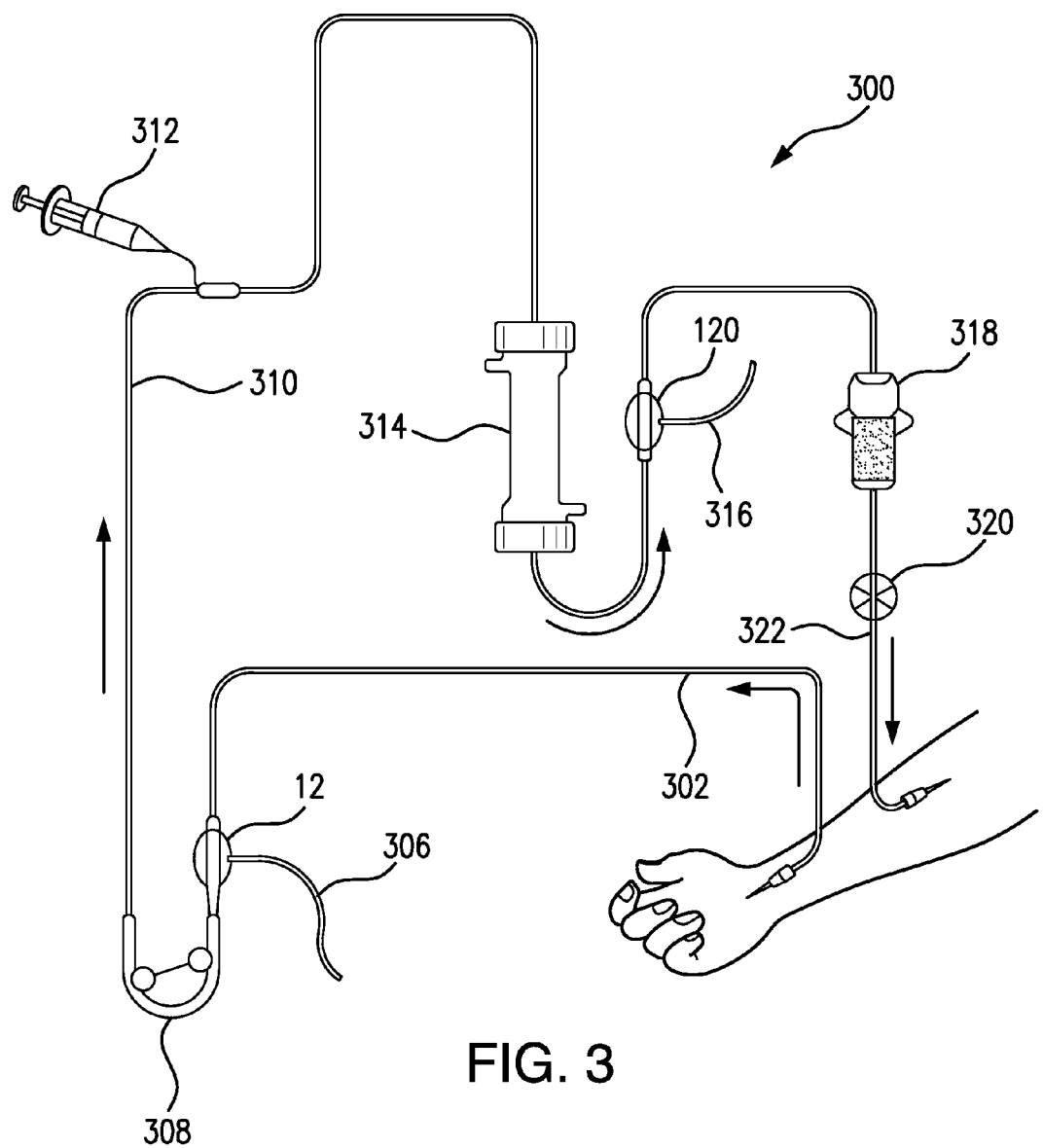
FIG. 3 shows the location of an arterial POD assembly and a venous POD assembly in an extracorporeal circuit of a hemodialysis machine, according to one or more embodiments of the present invention.

FIG. 3 is a schematic view of an extracorporeal blood circuit 300 for administration of hemodialysis. From a patient, a first arterial tubing 302 carries blood to an arterial POD assembly 12, for example, POD assembly 12 shown in FIGS. 1A-1C. A pressure tubing 306, connected to the sensor port of arterial POD assembly 12, directs a pressure output from POD assembly 12 to an arterial pressure port (not shown) of the hemodialysis machine. Blood flows through the flow-through chamber of POD assembly 12 to a blood pump 308, for example, a peristaltic blood pump. From blood pump 308 blood is moved through a tubing 310 to a dialyzer 314. Along tubing 310 a syringe pump 312 is provided, in fluid communication with tubing 310. Syringe pump 312 can be a heparin pump and can be configured to inject heparin into blood circuit 300. For the sake of simplification, dialysate tubings and a dialysate circuit are not shown connected to dialyzer 314.

Blood exiting dialyzer 314 travels through another segment of tubing to a venous POD assembly 120, for example, venous POD assembly 120 shown in FIGS. 2A-2C. A pressure tubing 316 in fluid communication with the sensor port of POD assembly 120, carries a pressure output to a venous pressure port (not shown) of the hemodialysis machine. Although FIG. 3 shows exemplary positions for arterial POD assembly 12 and venous POD assembly 120, it should be understood that the POD assemblies can be arranged at different locations along blood circuit 300. In one or more embodiments, venous POD assembly 120 is connected directly to the output of dialyzer 314. In FIG. 3 both arterial POD assembly 12 and venous POD assembly 120 are shown in a vertical orientation as opposed to a horizontal orientation, which can help prevent the accumulation and trapping of air bubbles within the POD assemblies.

Blood flowing through the flow-through chamber of venous POD assembly 120 exits POD assembly 120 and is carried along another segment of tubing to an air trap and air detector 318. Along a venous return tubing 322 that goes from air trap and air detector 318 to the patient, is arranged an air detector clamp 320 that can stop the return of blood to the patient in the event that air trap and air detector 318 detect air bubbles in the return blood line, i.e., in tubing 322.

Figure 4A:
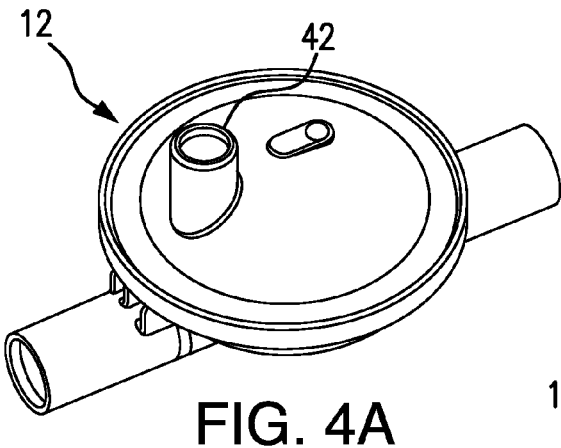
FIG. 4A is a top, left perspective view of an assembled POD, also referred to as a POD assembly, according to one or more embodiments of the present invention.
Figure 4B:
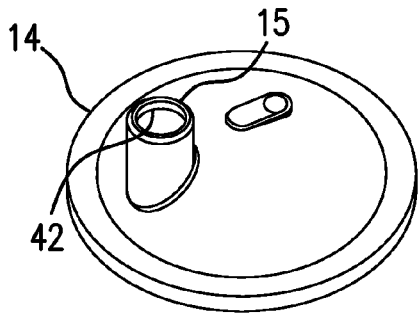
FIG. 4B is a top, left perspective view of the cap of the POD assembly shown in FIG. 4A.
Figure 4C:
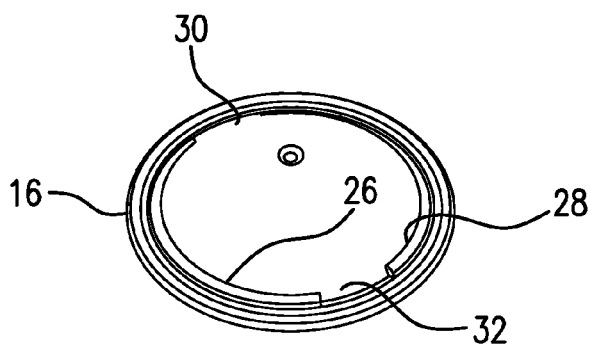
FIG. 4C is top, left perspective view of a diaphragm that can be used according to one or more embodiments of the present invention, and useful in the POD assembly shown in FIG. 4A.

As shown in FIGS. 4A-4E, a POD assembly 12 in accordance with one or more embodiments of the present invention, is provided. POD assembly 12 comprises a cap 14, a diaphragm 16, and a base 18. Diaphragm 16 can comprise a thermoplastic elastomer. Diaphragm 16 can be adhered, frictionally fit to, over-molded, or otherwise contacted onto or with cap 14. Cap 14 can be injection molded, for example, out of acrylonitrile butadiene styrene (ABS), another thermoplastic material such as polycarbonate, or the like. Base 18 can also be injection molded, for example, out of ABS, polycarbonate, or any other suitable thermoplastic material. Each cap 14, diaphragm 16, and base 18 can independently be three-dimensionally printed. Base 18 can be ultrasonically welded to cap 14 with a portion of diaphragm 16 compressed between base 18 and cap 14, to form a hermetic seal along a rim 20 of POD assembly 12. As seen in FIG. 4C, diaphragm 16 has two thin hinge features 26, 28, separated by two hinge interruptions 30, 32, which together allow smooth movement and flexibility of diaphragm 16 and accurate output of pressures, including venous pressures near zero. Cap 14 comprises a sensor port 15 that can be connected, for example, by solvent-bonding, to pressure tubing in fluid communication with a pressure port of a fluid processing machine, such as a hemodialysis machine.

Figure 4D:
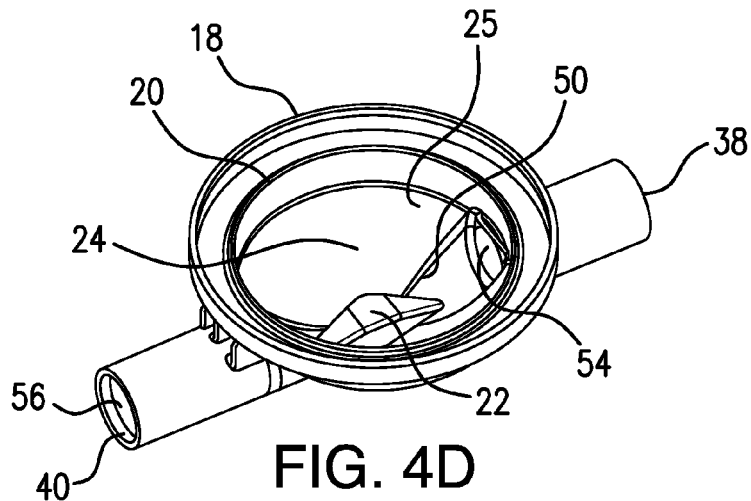
FIG. 4D is a top, left perspective view of the base of the POD assembly shown in FIG. 4A and showing a boss, according to one or more embodiments of the present invention, interrupting the flow path through the flow-through chamber of the POD assembly.
Figure 4E:
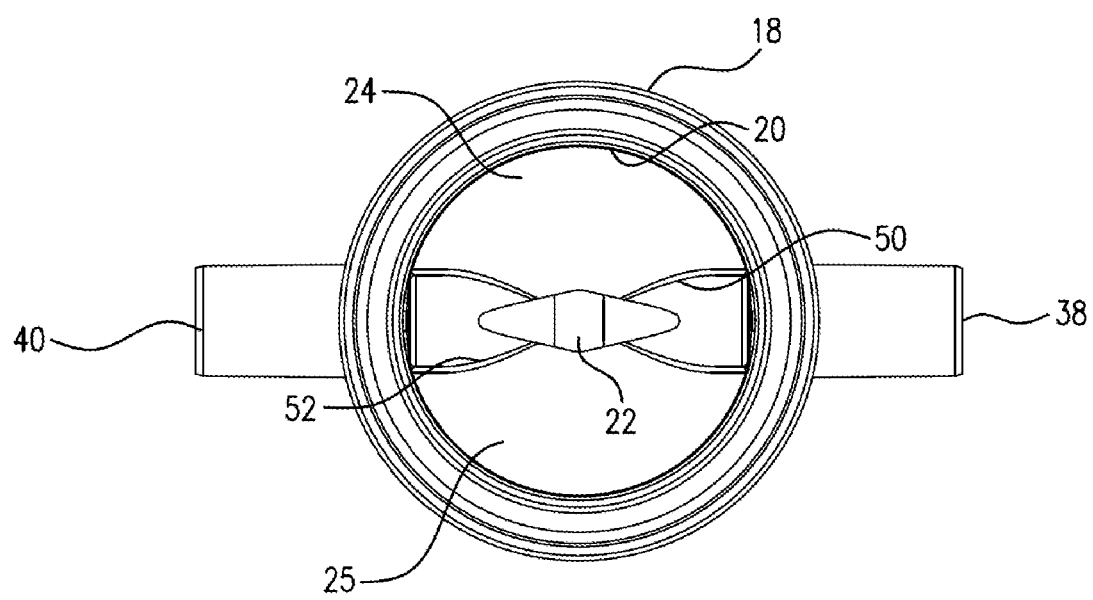
FIG. 4E is a top plan view looking down on the POD assembly base shown in FIG. 4D.

As seen in FIGS. 4D and 4E, base 18 has a diamond-shaped boss 22 extending from the central bottom area of base 18 toward the diaphragm in an assembled POD. Boss 22 reduces the potential for blood flow occlusion caused by the diaphragm contacting the internal surface of flow-through side or chamber 24. Boss 22 forms a discontinuance in an otherwise smooth bottom surface 25 of base 18. As best seen in FIG. 4E, smooth bottom surface 25 is interrupted not only by boss 22 but also by opposing cut-outs 50 and 52 that maintain the same bottom wall shape and depth as that provided by the bottom wall of flow path extensions 54 and 56, respectively, that are in fluid communication with inlet port 38 and outlet port 40, respectively (see also FIG. 6A).

Figure 5:
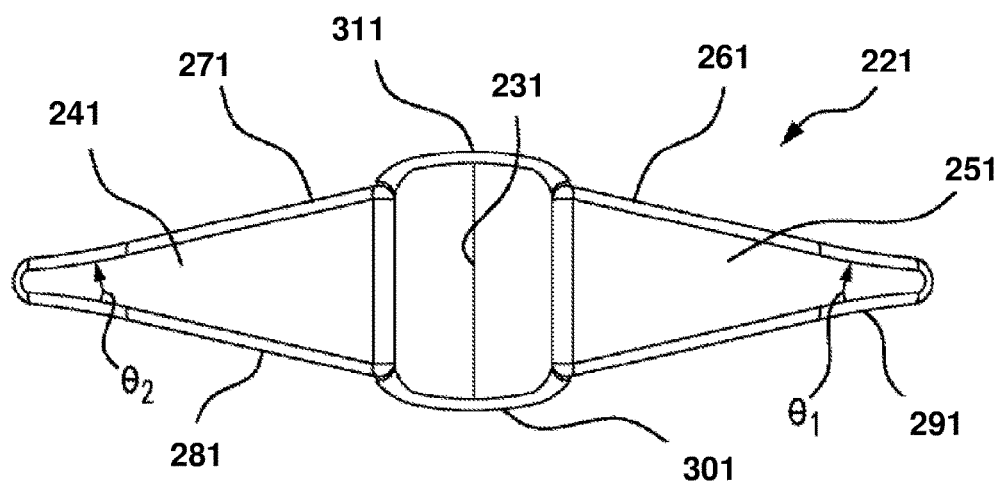
FIG. 5 is an enlarged view of an exemplary boss that can be formed in a POD assembly base, according to one or more embodiments of the present invention.
Figure 9A:
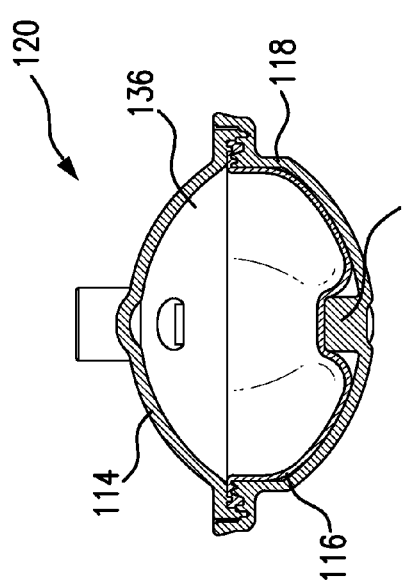
FIG. 9A is a cross-sectional side view of an arterial POD assembly according to one or more embodiments of the present invention, and showing the POD assembly diaphragm partially deformed around the boss at the bottom of the assembly base, due to a pressure fault condition.
Figure 9B:
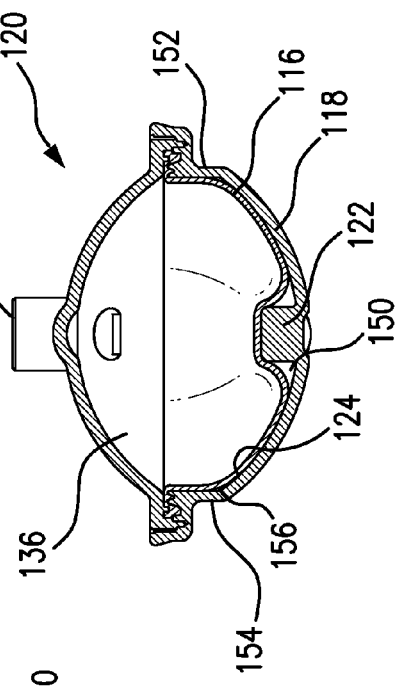
FIG. 9B is a cross-sectional side view of the arterial POD assembly shown in FIG. 9A.

FIG. 5 shows a top plan view of boss 221. Boss 221 has a top surface 231 that faces the diaphragm in an assembled POD, i.e., in a POD assembly. Under certain pressures, top surface 231 contacts the diaphragm. Top surface 231 is also referred to as a contacting surface and does not have to be the uppermost surface of boss 221. For example, in orientations where the POD assembly aligns the input and output ports of the flow-through chamber vertically, the top surface of the boss is also arranged vertically and is not the most vertically uppermost part of the boss. Top surface 231 can be flat, dome shaped, curved, sloped, channeled, grooved, a combination thereof, or the like. Boss 231 can have two sloped surfaces 241 and 251, as shown, that intersect with top surface 231 on opposite sides of top surface 231. The intersections can each independently be sharp, smooth, curved, angled, cornered, beveled, a combination thereof, or the like. Boss 221 can have side surfaces 261, 271, 281, and 291, as shown, each of which intersects with one of central sidewalls 301 and 311. The angle, $\theta_1$, at the intersection defined by sidewall 261 and 291, can be the same as or different than the angle, $\theta_2$, defined by the intersection of sidewalls 271 and 281. Angles $\theta_1$ and $\theta_2$ can each independently be within a range of from about 10° to about 40°, from about 15° to about 35°, or from about 20° to about 30°. In an exemplary embodiment, $\theta_1$ and $\theta_2$ are each 25.7°.

FIG. 6A is a cross-sectional side view of POD assembly 12 shown in FIG. 4A. FIG. 6B is an enlarged view showing the detail of section 6B taken from FIG. 6A. As can be seen, elastomeric diaphragm 16 is shown in its as-molded conformation. Elastomeric diaphragm 16 can be displaced by pressure and POD assembly 12 defines two chambers, 24 and 36, separated by diaphragm 16. Chamber 24 is the flow-through side or chamber of the device. Chamber 24 is in fluid communication with two access ports, including inlet port 38 and outlet port 40. Ports 38 and 40 can be solvent-bonded to tubing in an extracorporeal blood circuit, for example, in a hemodialysis circuit. During a dialysis treatment, blood flows through chamber 24 in a direction from inlet port 38, through flow path extension 54, through cut-out 50, through chamber 24, through cut-out 52, through flow path extension 56, and to outlet port 40.

Chamber 36, also called the pressure sensing side of the POD assembly, is in fluid communication with a sensor port 42. Sensor port 42 can be solvent-bonded to tubing that includes an attached female luer fitting at an opposite end thereof. The luer fitting provides a connection for POD assembly 12 to attach to the arterial or venous pressure port of a hemodialysis machine. The pressure port to which sensor port 42 is connected depends on the intended use and location of POD assembly 12.

According to one or more embodiments of the present invention, the monitor line or tubing that fits into and can be solvent-bonded to sensor port 42 can include an outer sleeve at the connecting end thereof. The sleeve can have an outer diameter that matches the inner diameter of sensor port 42. The sleeve can have an inner diameter that matches the outer diameter of the monitor line, for example, a diameter of 0.030 inch. As an example, the sleeve can be about 0.75 inch long and the monitor line can be about 11 inches long.

During a dialysis treatment, diaphragm 16 is displaced by pressure changes in the extracorporeal circuit. Displacement of the diaphragm increases or decreases the volume of air between the diaphragm and the pressure transducer in the hemodialysis machine. Changes in air volume produce changes in pressure against, or acting on, the pressure transducer. The POD assembly enables pressure monitoring of the extracorporeal circuit, without the need to have any air be in contact with blood in the circuit. The POD assembly can be specialized to output arterial circuit pressure, or venous circuit pressure, by setting the initial position of diaphragm 16 during manufacture of POD assembly 12. The diaphragm also prevents blood contamination of the pressure monitoring circuit in the dialysis machine, and prevents microbial contamination of the blood circuit. The flow-through side 24 and the pressure sensing side 36 are designed with internal volumes that facilitate accurate output of arterial pressures from 0 to −300 mmHg, and venous pressures from 0 to 500 mmHg, at elevations up to 8000 feet above sea level. Atmospheric pressure and chamber volumes can be directly related to a desired range of operation for accurate pressure output.

In one or more embodiments of the present invention, the POD assembly can include an interrupted hinge as part of the diaphragm. The amount of pressure required to overcome resistance to movement, of elastomeric diaphragm 16, affects the accuracy of the pressure output. As shown in FIG. 4C, two thin hinge features 26, 28 in the periphery of diaphragm 16 allow smooth diaphragm displacement with minimal loss of pressure output accuracy. Two hinge interruptions 30, 32 are provided to separate the two thin hinge features 26, 28. When diaphragm 16, of a venous POD assembly, is inverted to the zero pressure start position in pressure sensing side or chamber 36, the two hinge interruptions 30, 32 produce two small bulges along the wall of diaphragm 16. The bulges provide smooth flexibility and inverting of the diaphragm and enable accurate pressure output of venous pressures near zero, due to the fact that the bulges enable the diaphragm to exhibit very low resistance to displacement. Bulges are described in more detail below with reference to FIGS. 7A-8B.

When POD assembly 12 is connected to a pressure monitoring port, air pressure in flow-through side or chamber 24 slightly increases due to volume displacement. This volume displacement occurs as a seal is formed between the female luer connector of the POD assembly and the male luer of the hemodialysis machine. Other suitable connectors can be used and appropriate volume displacements can be compensated for depending on the connector type. The volume of air between diaphragm 16 and the pressure transducer in the hemodialysis machine is also susceptible to increases in temperature, which results in increased pressure. During a treatment, air temperature in chamber 36 increases due to blood flow, and heat can be generated by electronics inside the hemodialysis machine, for example, heat that can be at least partially trapped within a machine enclosure. The increased pressure caused by connecting the POD assembly to the hemodialysis machine and the increased pressure resulting from temperature increases during treatment can be compensated for by the low resistance-to-movement of the bulges. Without the bulges, the air pressure increase would add stress to diaphragm 16, and the stress in the diaphragm would translate to a small error in pressure output, particularly at pressures near zero. The inclusion of bulges obviates stress in the diaphragm and errors in pressure output.

FIGS. 6B and 6D are enlarged views of sections 6B and 6D shown, respectively, in FIGS. 6A and 6C. As can be seen, diaphragm 16 includes an outer peripheral grove 60 formed adjacent an outer peripheral wall 62 of diaphragm 16. The outer peripheral portion of diaphragm 16, including grove 60 and outer peripheral wall 62, is sandwiched between cap 14 and base 18 of POD assembly 12 (see FIGS. 6A and 6C). Cap 14 includes an outer peripheral shell rim 64 that is configured to fit into grove 60 of diaphragm 16. Outer peripheral shell rim 64 engages grove 60 and also provides an outer surface 66 that engages outer peripheral wall 62 of diaphragm 16. Cap 14 also includes an outer wall 68 that, together with outer peripheral shell rim 64, forms a grove 70 that is configured to accommodate and engage outer peripheral wall 62 of diaphragm 16. The interlocking arrangement between cap 14, diaphragm 16, and base 18, enable diaphragm 16 to be well seated and secured between cap 14 and base 18.

FIGS. 7A-10B shows a venous POD assembly 120, according to one or more embodiments of the present invention. POD assembly 120 comprises a cap 114, a diaphragm 116, and a base 118. Base 118 includes an inlet port 138 and an outlet port 140 that can be solvent-bonded to tubing in an extracorporeal venous blood circuit, for example, in a hemodialysis circuit. During dialysis treatment, blood flows through flow-through chamber 124 within the interior of POD assembly 120, in a direction from inlet port 138 toward and through outlet port 140. Cap 114 comprises a sensor port 141 that can be solvent-bonded to tubing that can fluidly connect sensor port 141 to a venous pressure port of a hemodialysis machine. Luer fittings can also or alternatively be used to connect any of the tubings to the POD assembly.

As shown in FIG. 7A, diaphragm 116 is at a treatment start position. A bulge 142 can be seen in diaphragm 116 and a similar bulge is provided in the other half (not shown) of diaphragm 116. Bulges 142 can be caused by hinge interruptions 130, 132 as shown in FIG. 7B. Hinge interruptions 130, 132 divide a peripheral hinge along the periphery of diaphragm 116 into two hinge features 126, 128. Greater details regarding hinge features 126, 128 and hinge interruptions 130, 132 can be discerned with reference to FIGS. 6B and 6D and the description of hinge feature 28 and hinge interruption 32 shown therein. In one or more embodiments, hinge features 126, 128 can be identical to hinge feature 28 described in FIG. 6B. In one or more embodiments, hinge interruptions 130, 132 can be identical to hinge interruptions 32 shown in FIG. 6D.

FIGS. 8A and 8B show venous POD assembly 120 illustrated in FIGS. 7A and 7B but wherein bulges 142, shown in FIGS. 7A and 7B, have been displaced and no longer exist along diaphragm 116. Locations 144 shown in FIGS. 8A and 8B indicate where bulges 142 had occurred in diaphragm 116, but are displaced due to a near zero pressure condition. Before being connected to a venous pressure port of the hemodialysis machine, bulges 142 can exist in diaphragm 116, but can be displacement upon connection of POD assembly 120 to the venous pressure port. The displacement can occur due to the very small increase in pressure within pressure-sensing side or chamber 136, resulting from the act of connecting the tubing from sensor port 141 of POD assembly 120 to the venous pressure port of the hemodialysis machine. Bulges 142 in diaphragm 116 can compensate for this very minor increase in pressure and can thus enable positioning of diaphragm 116 at the start of a treatment such that POD assembly 120 can very accurately measure a full range of expected pressures within the venous circuit.

With reference to FIGS. 7A-10B, a pressure output device (POD) assembly 120 is shown. POD assembly 120 can comprise a diamond-shaped boss 122 that can reduce, minimize, or substantially minimize the potential for hemolysis due to occlusion of blood flow through the POD assembly. As can be seen, diamond-shaped boss 122 extends into flow-through chamber 124. When POD assembly 120 is used to output negative pressure in an arterial blood circuit, fault conditions can displace diaphragm 116 into chamber 124 to an extent such that diaphragm 116 contacts and pushes below facing surface 123 of boss 122. When this occurs, diaphragm 116 partially deforms around boss 122 as shown in FIGS. 9A-10B, thus preventing diaphragm 116 from fully contacting an internal surface 125 of chamber 124. Without boss 122, diaphragm 116 could substantially fully and/or flushly contact internal surface 125. Full and flush contact would present various levels of occlusion to blood flow but such contact is avoided according to one or more embodiments of the present invention.

Figure 10A:
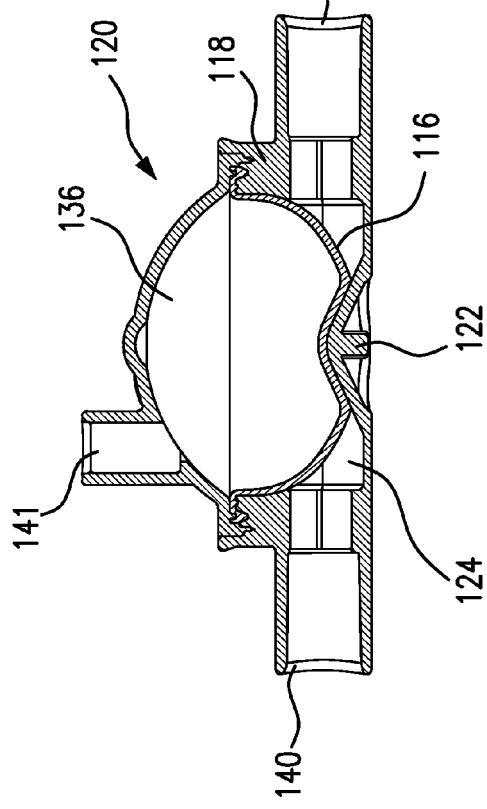
FIG. 10A is cross-sectional side view of the POD assembly shown in FIG. 9A but also showing how the base and boss provide a non-occluded blood flow path despite the pressure fault condition.
Figure 10B:
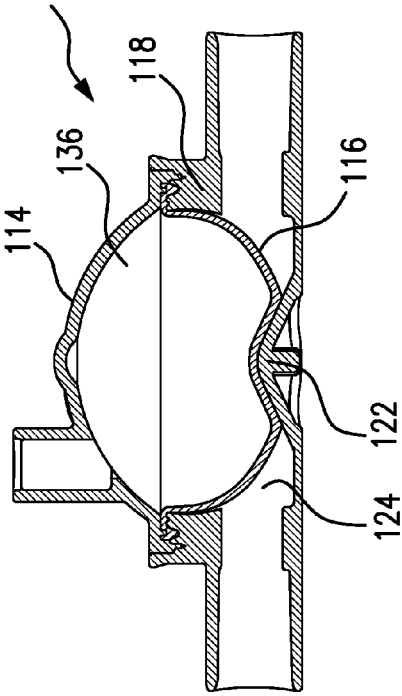
FIG. 10B is cross-sectional end view of the arterial POD assembly shown in FIG. 10A but at a pressure fault condition.

As can be seen in FIG. 10B, rather than occluding blood flow under the extreme pressure condition shown, boss 122 props-up, like a tent pole, diaphragm 116 and forms a blood flow path 150 arranged adjacent the side walls of boss 122 and through chamber 124, and boss 122 prevents occluding of blood flow path 150. Furthermore, the provision of vertical sidewall portions 152 and 154 in base 118 also provide flow-through spaces such as at 156 so that the blood flow path is not occluded.

Figure 11A:
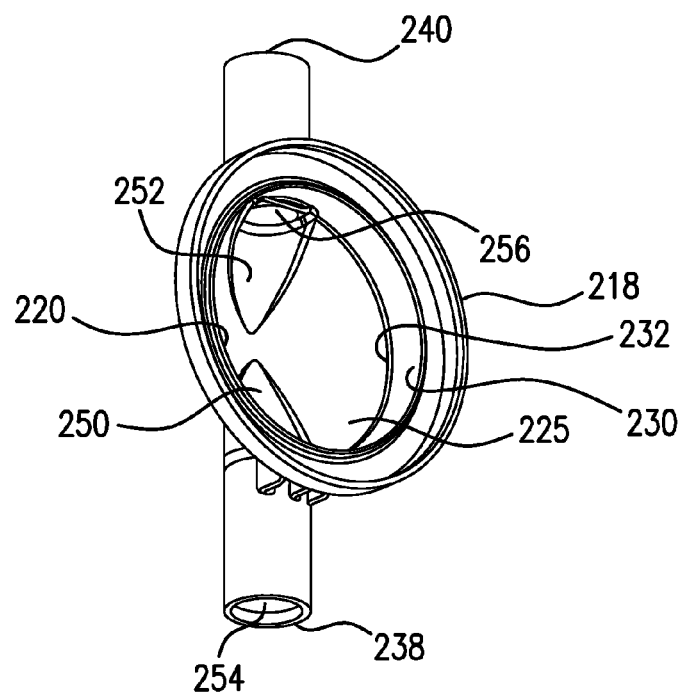
FIG. 11A is a top perspective view of the base of a POD assembly according to yet another embodiment of the present invention.
Figure 11B:
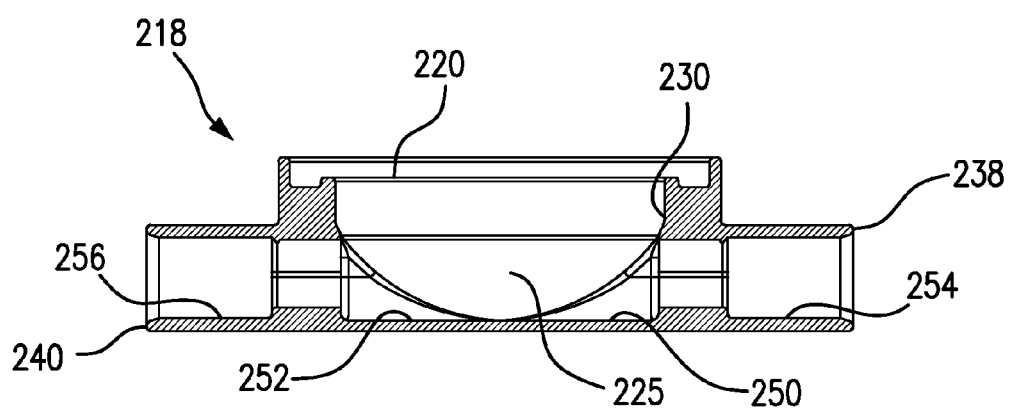
FIG. 11B is a cross-sectional, side view of the POD base shown in FIG. 11A.
Figure 11C:
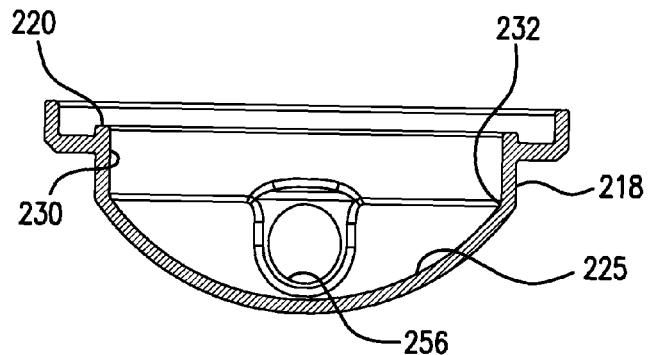
FIG. 11C is a cross-sectional, end view of the POD base shown in FIG. 11A.

As shown in FIGS. 11A-11C, a POD base 218, in accordance with one or more embodiments of the present invention, is provided. POD base 218 comprises an inlet port 238, an outlet port 240, a smooth bottom wall 225, a pair of opposing cut-outs, 250 and 252, formed in bottom wall 225, and flow path extensions 254 and 256, respectively, that are in fluid communication with inlet port 238 and outlet port 240, respectively. Cut-outs 250 and 252 each have a bottom that maintains the same bottom wall shape and depth as provided by the bottom of flow path extensions 254 and 256, respectively. Flow path extension 254 can have the same depth as cut-out 250 and the two features can be separated by a neck, as best seen in FIG. 11B. Similarly, flow path extension 256 can have the same depth as cut-out 252 and the two features can be separated by a neck. Blood tubing having an outer diameter that is the same as the inner diameter of a flow path extension can be inserted into the flow path extension and solvent bonded therein.

Figure 11D:
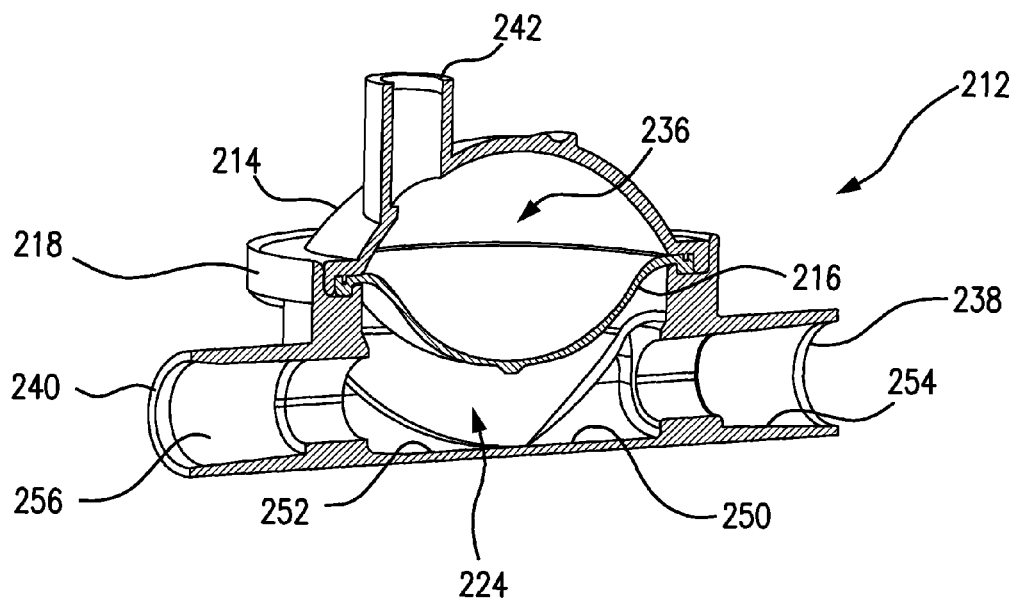
FIG. 11D is a cross-sectional, left perspective side view of an assembled POD according to an embodiment of the present invention, and including the POD base shown in FIGS. 11A-11C.
Figure 11E:
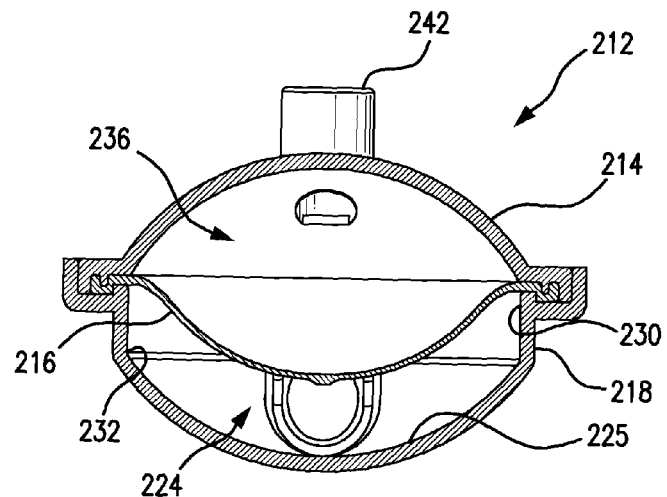
FIG. 11E is a cross-sectional, end view of the POD assembly shown in FIG. 11D.

POD base 218 can be provided with a vertical wall extension 230. Smooth bottom wall 225 intersects with vertical wall extension 230 along a circle 232. As can be seen in FIGS. 11D and 11E, POD base 218 can be assembled with a cap 214 and a diaphragm 216 to form a POD assembly 212 defining a flow-through chamber 224 and a pressure sensing chamber 236. Vertical wall extension 230 can be of any suitable height, and can be included to maintain a diaphragm, such as diaphragm 216 shown in FIGS. 11D and 11E, above and spaced from bottom wall 225, for example, to prevent diaphragm 216 from contacting bottom wall 225 and occluding flow through flow-through chamber 224 of POD assembly 212. As shown, cut-outs 250 and 252 can be formed completely in bottom wall 225, and not in vertical wall extension 230. In some embodiments, the cut-outs can also be defined, at least in-part, by vertical wall extension 230.

A rim 220 is formed near the outer periphery of POD base 218, which can form a hermetic seal with a diaphragm, as shown in the assembled POD assembly illustrated in FIGS. 11D and 11E. POD base 218 can be injection molded, for example, out of ABS, polycarbonate, or any other suitable thermoplastic material. POD base 218 can be three-dimensionally printed. POD base 218 can be ultrasonically welded to cap 214, as shown in FIGS. 11D and 11E, with the periphery of diaphragm 216 compressed between POD base 218 and cap 214, to form a hermetic seal along rim 220. Cap 214 comprises a sensor port 242 that can be connected, for example, by solvent-bonding, to pressure tubing that can be made to be in fluid communication with a pressure port of a fluid processing machine, such as a hemodialysis machine.

Figure 12A:
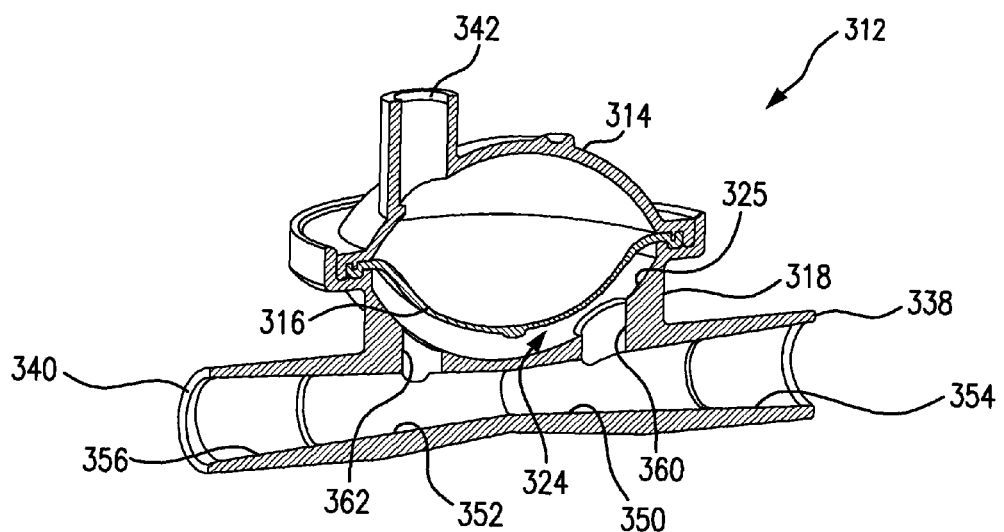
FIG. 12A is a cross-sectional, left perspective side view of a POD assembly according to yet another embodiment of the present invention.
Figure 12B:
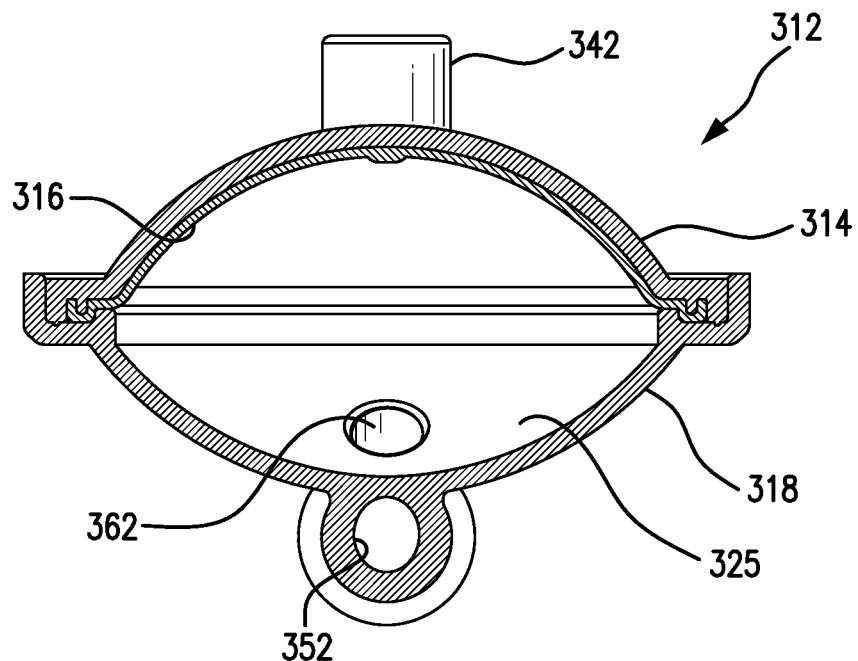
FIG. 12B is cross-sectional, end view of the POD assembly shown in FIG. 12A, but wherein the POD assembly is configured for arterial measurement and is shown at zero (0) arterial pressure.
Figure 12C:
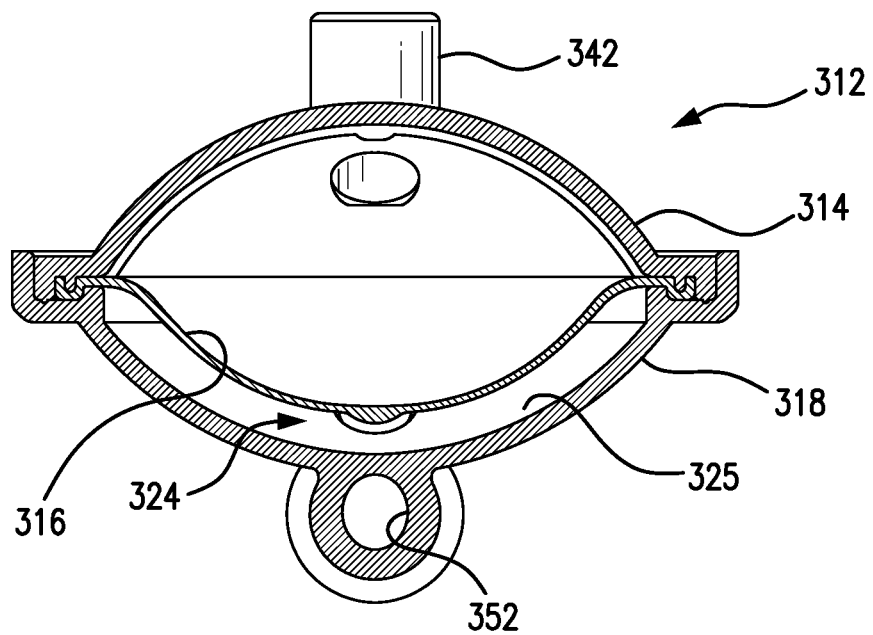
FIG. 12C is cross-sectional, end view of the POD assembly shown in FIG. 12A, and wherein, as also shown in FIG. 12A, the POD assembly is configured for use as a venous POD assembly and the diaphragm is shown at zero (0) venous pressure.

FIGS. 12A-12C show yet another POD assembly according to one or more embodiments of the present invention, and configured to monitor venous pressure. In FIGS. 12A-12C, a POD assembly 312, in accordance with one or more embodiments of the present invention, is shown. POD assembly 312 includes a POD base 318, a POD cap 314, and a diaphragm 316 pinched and held between POD base 318 and POD cap 314. POD base 318 comprises an inlet port 338, an outlet port 340, a smooth bottom wall 325, flow path extensions 354 and 356, bypass channel portions 350 and 352, an inlet chamber port 360, and an outlet chamber port 362. Flow path extensions 354 and 356 are in fluid communication with inlet port 338 and outlet port 340, respectively. A bypass channel is provided that comprises flow path extension 354, bypass channel portion 350, bypass channel portion 352, and flow path extension 356. Inlet chamber port 360 is in fluid communication with bypass channel portion 350 and a flow-through chamber 324 defined between POD base 318 and diaphragm 316. Outlet chamber port 362 is in fluid communication with bypass channel portion 352 and flow-through chamber 324. While blood can flow into and out of flow-through chamber 324, blood can also bypass chamber 324 through the bypass channel. In the event of an occlusion of flow through flow-through chamber 324, blood can still flow into inlet port 338 and out outlet port 340. Cap 314 comprises a sensor port 342 that can be connected, for example, by solvent-bonding, to pressure tubing that can be made to be in fluid communication with a pressure port of a hemodialysis machine.

As can be seen best in FIG. 12A, bypass channel portion 350 narrows from its intersection with flow path extension 354 toward its intersection with bypass channel portion 352. Similarly, bypass channel portion 352 narrows from its intersection with flow path extension 356 toward its intersection with bypass channel portion 350. The narrowing of the bypass channel portions influences the flow of blood through the bypass channel such that a portion of the flow is directed into flow-through chamber 324 and the pressure of blood flowing through the bypass channel and through flow-through chamber 324 can be sensed.

FIG. 12B shows the same POD assembly 312 shown in FIGS. 12A and 12C, but wherein the diaphragm is positioned adjacent the inside of cap 314 such that the POD assembly is configured for sensing arterial pressure. FIG. 12C is a cross-sectional end view of FIG. 12A, wherein, just as is shown in FIG. 12A, POD assembly 312 is configured for sensing venous pressure.

Figure 13:
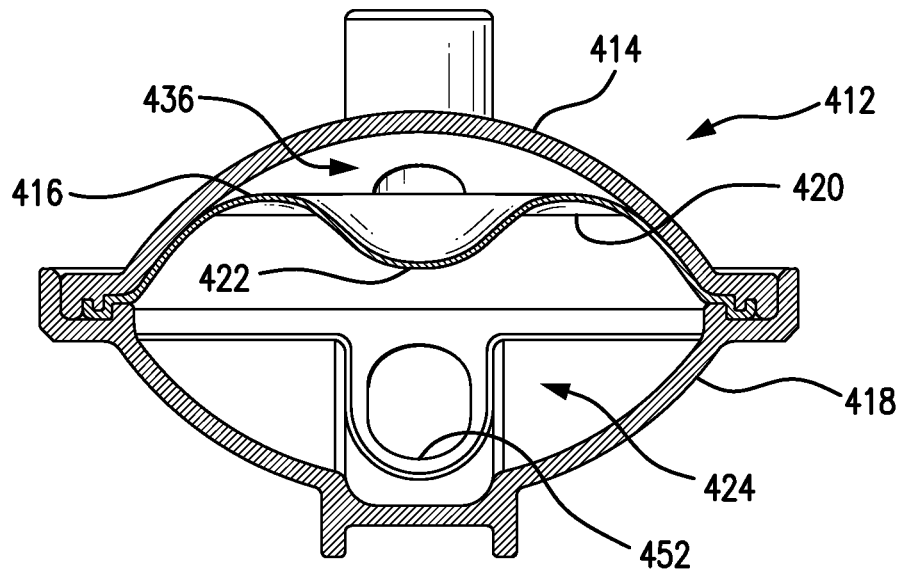
FIG. 13 is a cross-sectional, end view of yet another POD assembly according to the present invention, configured to sense arterial pressure, and including a telescoping diaphragm shown under zero (0) arterial pressure.

FIG. 13 shows yet another POD assembly according to one or more embodiments of the present invention, and configured for sensing arterial pressure. In FIG. 13, a POD assembly 412 is shown and comprises a cap 414, a base 418, and a telescoping diaphragm 416 pinched and held between cap 414 and base 418. Diaphragm 416 separates the interior of POD assembly 412 into a flow-through chamber 424 below the diaphragm and a pressure sensing chamber 436 above the diaphragm. Flow-through chamber 424 is in fluid communication with an inlet and an outlet, and the outlet shown includes a flow path extension 452. Diaphragm 416 includes a circular hinge 420 defining a circle at which a top dome 422 of diaphragm 416 can pivot between a popped-in configuration as shown and a popped-out configuration (not shown) where dome 422 is adjacent the inside top surface of cap 414. Hinge 420 enables a smooth change between the popped-in and popped-out configurations so that pressure can be accurately sensed even in pressure ranges just below or just above the pressures that cause a popping-in or a popping-out action. Thus, accurate arterial pressures can be sensed over the entire range of arterial pressures to which the diaphragm is expected to be exposed during a hemodialysis treatment.

Figure 14:
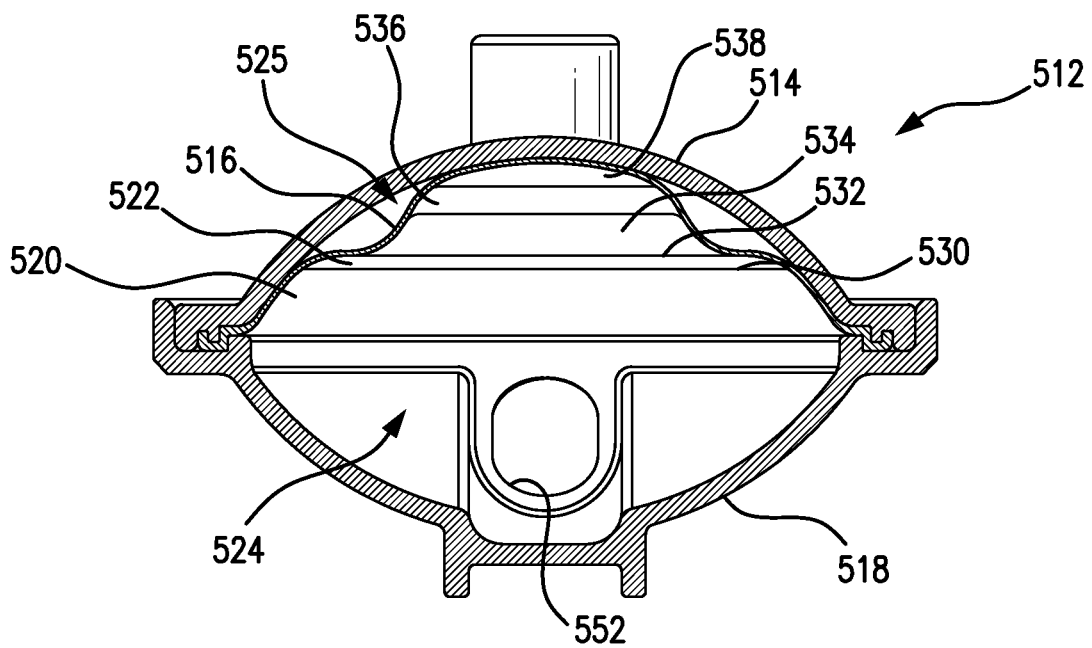
FIG. 14 is a cross-sectional, side view of a POD assembly according to yet another embodiment of the present invention, configured to sense arterial pressure, and including a telescoping diaphragm shown at zero (0) arterial pressure.
Figure 15:
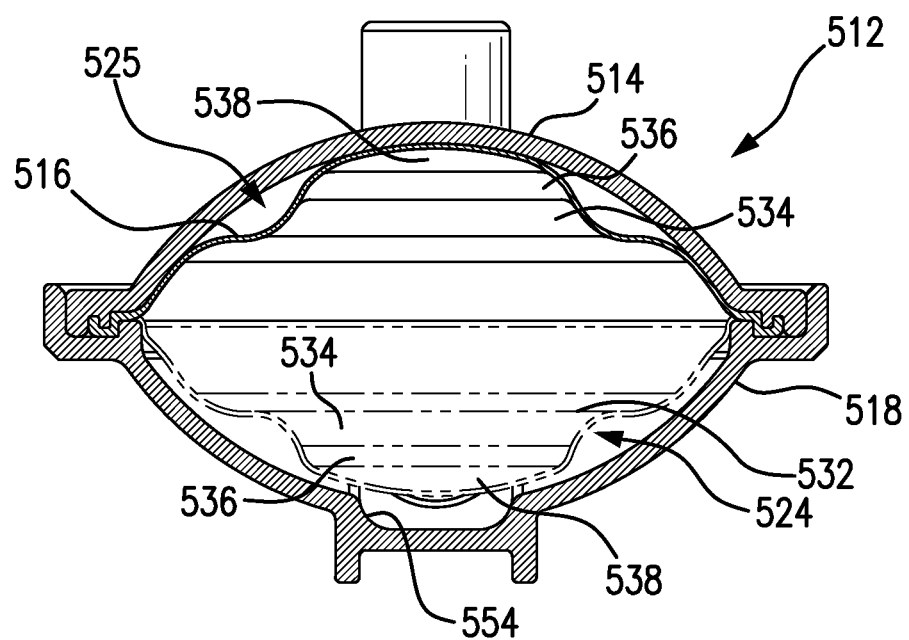
FIG. 15 is a cross-sectional, end view of the pressure POD assembly shown in FIG. 14 but demonstrating the two alternative starting positions of the diaphragm, including an upper position to be used if the POD assembly is configured as an arterial pressure POD assembly, and including the lower position to be used if the POD assembly is configured as a venous pressure POD assembly.

FIGS. 14 and 15 show yet another POD assembly according to one or more embodiments of the present invention. In FIG. 14, POD assembly 512 is configured for sensing arterial pressure. In FIG. 15, two alternative starting positions of the diaphragm are shown. POD assembly 512 comprises a cap 514, a base 518, and a telescoping diaphragm 516 pinched and held between cap 514 and base 518. Diaphragm 516 separates the interior of POD assembly 512 into a flow-through chamber 524 below the diaphragm and a pressure sensing chamber 525 above the diaphragm. Flow-through chamber 524 is in fluid communication with an inlet and an outlet, and the outlet shown includes a flow path extension 552. Diaphragm 516 includes a plurality of circular hinges, including hinges 530 and 532, which define respective circles at which one or more segments of diaphragm 516 can pivot. For example, diaphragm 516 can be divided into a base segment 520, intermediate segments 522, 534, and 536, and a top segment or dome 538. Segments 520 and 522 can pivot with respect to one another along hinge 530. Segments 522 and 534 can pivot with respect to one another along hinge 532. The entirety of diaphragm 516 can also be inverted, as shown by the bottom diaphragm position illustrated in FIG. 15.

The plurality of segments and plurality of hinges enable a smooth change between popped-in and popped-out configurations so that pressure can be accurately sensed even in pressure ranges just below or just above the pressures that cause a popping-in or a popping-out action. Thus, for the arterial configuration, specifically, as shown in FIG. 14, accurate arterial pressures can be sensed over the entire range of arterial pressures to which the diaphragm is expected to be exposed during a hemodialysis treatment. For the venous configuration, specifically, as shown in FIG. 15 with the diaphragm at the bottom position, accurate venous pressures can be sensed over the entire range of venous pressures to which the diaphragm is expected to be exposed during a hemodialysis treatment.

According to one of more embodiments of the present invention, the diaphragm position within the POD assembly can be adjusted and set such that a user can set the amount of negative versus positive pressure that the POD assembly can sense. A pressure monitoring machine, for example, a hemodialysis machine, can be provided with a pneumatic cylinder that is in fluid communication with the pressure sensing chamber or side of the POD assembly. A three-way valve can be provided in fluid communication with the pneumatic cylinder and can be opened to enable the pressure within the pneumatic cylinder to equilibrate with the surrounding ambient air pressure. The pneumatic cylinder can have a greater volume than the volume inside the interior of the POD assembly, for example, at least 1.5 times as large, or at least two times as large, as the interior volume of the POD assembly. A piston within the pneumatic cylinder can be placed at a mid-point position. The three-way valve can then be closed to isolate the pneumatic cylinder from the surrounding environment, to enable the pneumatic cylinder to be in pneumatic contact with the POD assembly diaphragm, and to form a fluid communication between the pneumatic cylinder and the pressure sensing chamber of the POD assembly. Next, the piston within the cylinder can be advanced until a pressure gauge reading of 1 psi is achieved, at which point the position of the piston within the cylinder can be recorded. The piston can be then retracted in the cylinder until the pressure gauge achieves a reading of −1 psi, at which point the piston position can be recorded. The mid-point between the two recorded positions of the piston within the pneumatic cylinder can be established as a mid-point of the POD assembly diaphragm. The diaphragm can be positioned accordingly and the three-way valve can be closed-off to preserve the position of the diaphragm. Other positions of the piston, positions aligned with graduated indicia, or the like, can be used to calibrate the POD assembly diaphragm position and enable accurate pressure sensing over a desired pressure range.

According to one or more embodiments of the present invention, a pair of POD assemblies, one for sensing arterial pressure and one for sensing venous pressure, can be included in a blood tubing set that is intended to be used with a Fresenius Medical Care 2008® Series K, K2, or T Hemodialysis Machine. The POD assemblies shown in FIGS. 1A-2C and 4A-10B are exemplary. The machine can be equipped with a level detector module for standard air-detection compliance and equipped with an air detector module for enhanced micro-bubble detection compliance. The bloodline can be part of an extracorporeal circuit by which blood is transported from the patient through a hemodialyzer (for cleansing), and back to the patient. The pump segment in the bloodline interfaces to the blood pump rotor mechanism on the hemodialysis machine, which drives the flow of blood through the circuit. The bloodline contains interfaces to the hemodialysis machine safety mechanism to ensure proper operation. These interfaces can be for POD monitor lines for monitoring arterial and venous pressures, as well as for a venous chamber for the detection of air in the blood path. The Arterial pressure measurement POD can be mounted flush with the inlet-side pump housing.

In use, an operator can calibrate the blood pump for 8 mm pump segments according to the 2008® Series K, K2, and T Hemodialysis Machine Operator's Instructions. The actual blood flow rate may differ from the blood flow rate indicated by the machine and may change with time. Actual blood flow is affected by arterial and venous pressures, hematocrit, AV fistula needle size, and other factors.

To spike a saline bag, the operator can remove the spike protector without touching the spike and insert the spike through the port on the saline bag. Prior to priming, the operator can ensure that the POD flexible diaphragms are in their correct positions. In general, the arterial diaphragm is curved towards the dome side or cap of the POD. The venous diaphragm is curved towards the base side of the POD.

To correct a mis-positioned diaphragm, a 5 mL (or larger) syringe can be used to inject or extract air though the pressure tubing or monitor line to move the diaphragm to the appropriate position. The diaphragm may readjust slightly when the syringe is removed.

During treatment, the arterial POD can run approximately full to ½ full, and the venous POD can run approximately ¼ full to ¾ full. The POD diaphragms will pulsate and change position slightly during treatment. Significant diaphragm position changes can cause incorrect pressure readings and can require corrective action. An operator can correct a diaphragm if either the arterial or venous diaphragm contacts the base or boss, or if the venous diaphragm contacts greater than ¾ of the dome surface during diaphragm pulsation.

To correct a mis-positioned arterial diaphragm during treatment due to an arterial pressure alarm or a zero arterial pressure reading, the following steps can be taken. The operator can stop the blood pump, close the arterial patient clamp, and reset the alarms if necessary. The operator can disconnect the arterial monitor line from the machine pressure port and allow the diaphragm to return to its correct position. Saline administration and saline "T" clamps can be opened if necessary. The operator can reattach the monitor line to the machine pressure port and close the saline administration and saline "T" clamps. The operator can then open the arterial patient clamp, restart the blood pump, and observe to verify the correct diaphragm position and appropriate pressure reading. After making an arterial POD diaphragm adjustment, the operator can ensure that the arterial monitor line connection to the machine port is secure.

To correct a mis-positioned venous diaphragm during treatment due to a venous pressure alarm, a TMP alarm, or a zero venous pressure reading, the following steps can be taken. The operator can press Reset to reset the alarm, stop the blood pump, press the Reset key again, and hold it for two seconds to select new alarm limits. The operator can press the ▼level key on the machine venous module until the diaphragm is positioned to just touch the base side boss and then use the ▲level adjust key to then move the diaphragm back slightly until it no longer touches the boss. Then, the operator can restart the blood pump and observe to verify the correct diaphragm position and appropriate pressure reading.

In some cases, to correct a mis-positioned venous diaphragm during treatment due to a venous pressure alarm, a TMP alarm or a zero venous pressure reading, the following steps can be taken. The operator can stop the blood pump, close the venous monitor line clamp, and reset the alarms if necessary. The operator can disconnect the venous monitor line from machine pressure port, connect a 5 mL (or larger) syringe, with plunger pulled back, to the venous monitor line, open the monitor clamp, and inject up to 4 mL of air until the diaphragm is positioned to just touch the base side boss. The operator can pull back on the plunger to then move the diaphragm back slightly until it no longer touches the boss. After that, the operator can close the monitor line clamp, remove the syringe, reattach the monitor line to the machine pressure port, open the clamp, and restart the pump. The operator can then observe to verify the correct diaphragm position and appropriate pressure reading. After making venous POD diaphragm adjustments the operator can ensure the venous monitor line connection to the machine port is secure.

The dialyzer can be primed according to the machine manufacturer's instructions. If the instructions require clamping bloodlines, the pressure-monitoring lines should be unclamped before occluding the bloodlines, to prevent excessive dialyzer pressures.

The venous chamber fluid level can be established by purging air through a venous chamber "pigtail" access site. An operator can open the "pigtail" clamp and loosen the cap. When air is removed, and both the chamber and "pigtail" are full, the operator can then clamp the line and tighten the cap.

To set up the blood lines, an operator can first ensure the Dialyzer Holder Lock Sleeve is installed onto the dialyzer holder in accordance with the Dialyzer Holder Lock Sleeve mounting instructions for the machine. The operator can push the dialyzer into the holder, arterial end down, with the clamp in the middle of the dialyzer, then position the dialysate ports to the right, facing outwardly away from the machine.

For the arterial line, the operator can close the heparin line clamp, then ensure the arterial POD diaphragm is correctly positioned toward the dome side or cap. The blood pump segment can then be inserted into the blood pump. The operator can ensure the segment with the arterial POD is threaded to the left side of the blood pump housing with the monitoring line facing forward, away from the machine. The machine door can then be closed. Next, the operator can connect the dialyzer end of the arterial line to the bottom/arterial port of the dialyzer, and ensure the connection to the port is finger tight. The operator can then aseptically place the patient end of the arterial line into a priming bucket clip.

For the venous line, the operator can close the venous chamber "pigtail" access site clamp. The operator can ensure the venous POD diaphragm is correctly positioned toward the base side of the POD. Next, the operator can roll the venous drip chamber into the venous level detector with the filter located below the sensor heads. Next, the operator can connect the dialyzer end of the venous line to the top/venous port of the dialyzer, and position the venous POD so that the dome side or cap is facing forward. The operator can ensure the connection to the port is finger tight. Next, the operator can clamp the venous POD monitor line, leave it disconnected from the machine, and aseptically place the patient end of the venous line into the priming bucket clip. Priming of the extracorporeal circuit can require approximately 300 mL of saline, depending on the size and model of the dialyzer.

During treatment, the arterial and venous pressures can be routinely monitored. Pressure readings which are clinically inappropriate (e.g. 0 mmHg) can be addressed immediately as these may indicate a POD monitor line is clamped, kinked, not attached securely, or that the POD diaphragm is not in the correct position.

The present invention includes the following numbered aspects, embodiments, and features, in any order and/or in any combination:

1. A pressure output device for sensing fluid pressure in a fluid processing system, the pressure sensing device comprising:
   a shell defining a shell interior; and
   a movable diaphragm disposed in the shell interior and separating the shell interior into a flow-through chamber defined by a lower portion of the shell and a first side of the diaphragm, and a pressure sensing chamber defined by an upper portion of the shell and a second side of the diaphragm, the second side being opposite the first side, the shell further defining a sensor port in fluid communication with the pressure sensing chamber, an inlet port in fluid communication with the flow-through chamber, and an outlet port in fluid communication with the flow-through chamber,
   wherein the inlet port and the outlet port define an inlet and an outlet, respectively, of a fluid flow path through the flow-through chamber, and the flow-through chamber has an interior wall and comprises a boss along the interior wall, which prevents the diaphragm from occluding flow through the fluid flow path.

2. The pressure output device of any preceding or following embodiment/feature/aspect, wherein the inlet port has an axial center, the outlet port has an axial center, the axial center of the inlet port is substantially or completely aligned with the axial center of the outlet port, the boss protrudes from the interior wall and extends into the fluid flow path, and the boss includes at least one feature that intersects with a line that is co-axial with one or both of the axial centers.

3. The pressure output device of any preceding or following embodiment/feature/aspect, wherein the fluid processing system is a hemodialysis machine, the fluid path is a blood path, and the boss comprises a diamond-shaped cross-section configured to minimize the potential for hemolysis due to occlusion of blood flow.

4. The pressure output device of any preceding or following embodiment/feature/aspect, wherein the boss comprises a mid-section, a first end adjacent the inlet port, and a second end adjacent the outlet port, and the boss has a thickness that increases in a direction from the first end toward the mid-section and a thickness that increases in a direction from the second end toward the mid-section.

5. The pressure output devices of any preceding or following embodiment/feature/aspect, wherein the boss has a width that increases in a direction from the first end toward the mid-section and a width that increases in a direction from the second end toward the mid-section.

6. A system comprising the pressure output device of any preceding or following embodiment/feature/aspect, a pressure monitor, and a monitor line that forms a fluid communication between the sensor port and the pressure monitor.

7. A system comprising the pressure output device of any preceding or following embodiment/feature/aspect, a first blood tubing in fluid communication with the inlet port, a second blood tubing in fluid communication with the outlet port, and a blood pump in operative engagement with at least one of the first blood tubing and the second blood tubing.

8. The pressure output device of any preceding or following embodiment/feature/aspect, wherein the shell comprises a shell top and a shell bottom, the movable diaphragm comprises an outer periphery, and the outer periphery is sandwiched between the shell top and the shell bottom.

9. The pressure output device of any preceding or following embodiment/feature/aspect, wherein the outer periphery of the movable diaphragm includes a groove, and at least one of the shell top and the shell bottom includes an outer peripheral shell rim configured to fit into the groove and engage the outer periphery of the movable diaphragm.

10. The pressure output device of any preceding or following embodiment/feature/aspect, wherein the shell top and the shell bottom are bonded together, the movable diaphragm is positioned between the shell top and the shell bottom, and the outer peripheral rim is seated in the groove of the movable diaphragm.

11. The pressure output device of any preceding or following embodiment/feature/aspect, wherein the groove is formed on a first side of the movable diaphragm, the outer periphery of the movable diaphragm comprises a rim along a second side of the movable diaphragm opposite the first side, the shell top comprises the outer peripheral shell rim, and the shell bottom comprises an outer peripheral groove configured to accommodate and engage the rim of the movable diaphragm.

12. The pressure output device of any preceding or following embodiment/feature/aspect, wherein the diaphragm comprises a peripheral hinge and one or more hinge interruptions that form one or more respective discontinuances along the peripheral hinge.

13. A pressure output device for sensing fluid pressure in a fluid processing system, the pressure sensing device comprising:
   a shell defining a shell interior; and
   a movable diaphragm disposed in the shell interior and separating the shell interior into a flow-through chamber defined by a lower portion of the shell and a first side of the diaphragm, and a pressure sensing chamber defined by an upper portion of the shell and a second side of the diaphragm, the second side being opposite the first side, the shell further defining a sensor port in fluid communication with the pressure sensing chamber, an inlet port in fluid communication with the flow-through chamber, and an outlet port in fluid communication with the flow-through chamber, the inlet port and the outlet port being aligned with one another along a first line,
   wherein the inlet port and the outlet port define an inlet and an outlet, respectively, of a fluid flow path through the flow-through chamber, the flow-through chamber comprises an interior shell wall having a mid-section that includes a smooth uninterrupted surface that is continuous from a first point on the interior shell wall at a first intersection with the diaphragm to a second point on the interior shell wall at a second intersection with the diaphragm, the first and second points are arranged along a line that is perpendicular to the first line, the inlet of the fluid flow path merges with the smooth uninterrupted surface of the interior shell wall at a first partial interior shell wall cut-out, the outlet of the fluid flow path merges with the smooth uninterrupted surface of the interior shell wall at a second partial interior shell wall cut-out, the fluid flow path includes the first partial interior shell wall cut-out, the interior shell wall mid-section, and the second partial interior shell wall cut-out, and the first and second interior shell wall cut-outs do not intersect with one another.

14. The pressure output device of any preceding or following embodiment/feature/aspect, wherein the inlet port has an axial center, the outlet port has an axial center, and the axial center of the inlet port is substantially or completely aligned with the axial center of the outlet port.

15. The pressure output device of any preceding or following embodiment/feature/aspect, wherein the fluid processing system is a hemodialysis machine, the fluid flow path is a blood flow path, and the fluid flow path is configured to minimize the potential for hemolysis due to occlusion of blood flow.

16. A system comprising the pressure output device of any preceding or following embodiment/feature/aspect, a pressure monitor, and a monitor line that forms a fluid communication between the sensor port and the pressure monitor.

17. A system comprising the pressure output device of any preceding or following embodiment/feature/aspect, a first blood tubing in fluid communication with the inlet port, a second blood tubing in fluid communication with the outlet port, and a blood pump in operative engagement with at least one of the first blood tubing and the second blood tubing.

18. The pressure output device of any preceding or following embodiment/feature/aspect, wherein the shell comprises a shell top and a shell bottom, the movable diaphragm comprises an outer periphery, and the outer periphery is sandwiched between the shell top and the shell bottom.

19. The pressure output device of any preceding or following embodiment/feature/aspect, wherein the outer periphery of the movable diaphragm includes a groove, and at least one of the shell top and the shell bottom includes an outer peripheral shell rim configured to fit into the groove and engage the outer periphery of the movable diaphragm.

20. The pressure output device of any preceding or following embodiment/feature/aspect, wherein the shell top and the shell bottom are bonded together, the movable diaphragm is positioned between the shell top and the shell bottom, and the outer peripheral rim is seated in the groove of the movable diaphragm.

21. The pressure output device of any preceding or following embodiment/feature/aspect, wherein the groove is formed on a first side of the movable diaphragm, the outer periphery of the movable diaphragm comprises a rim along a second side of the movable diaphragm opposite the first side, the shell top comprises the outer peripheral shell rim, and the shell bottom comprises an outer peripheral groove configured to accommodate and engage the rim of the movable diaphragm.

22. A pressure output device for sensing fluid pressure in a fluid processing system, the pressure sensing device comprising:
   a shell defining a shell interior; and
   a movable diaphragm disposed in the shell interior and separating the shell interior into a flow-through chamber defined by a lower portion of the shell and a first side of the diaphragm, and a pressure sensing chamber defined by an upper portion of the shell and a second side of the diaphragm, the second side being opposite the first side, the shell further defining an interior bottom wall of the flow-through chamber, a sensor port in fluid communication with the pressure sensing chamber, a bypass channel separated from the flow-through chamber and formed underneath the interior bottom wall, an inlet chamber port that forms a first fluid communication between the flow-through chamber and the bypass channel, and an outlet chamber port that forms a second fluid communication between the flow-through chamber and the bypass channel,
   wherein the bypass channel comprises an inlet port adjacent the inlet chamber port and configured to connect to an incoming blood line, and an outlet port adjacent the outlet chamber port and configured to connect to an outgoing blood line, and the bypass channel provides a non-occluded blood flow path from the inlet port to the outlet port even if the diaphragm completely occludes blood flow through the flow-through chamber.

23. The pressure output device of any preceding or following embodiment/feature/aspect, wherein the bypass channel has a first diameter at the inlet port and a second, smaller diameter, between the inlet chamber port and the outlet chamber port.

24. The pressure output device of any preceding or following embodiment/feature/aspect, wherein the bypass channel has a third diameter at the outlet port, which is larger than the second diameter between the inlet chamber port and the outlet chamber port.

25. A system comprising the pressure output device of any preceding or following embodiment/feature/aspect, and a hemodialysis machine, the hemodialysis machine comprising a pressure monitor, wherein the system further comprises a pressure monitor line that forms a fluid communication between the sensor port and the pressure monitor.

26. A system comprising the pressure output device of any preceding or following embodiment/feature/aspect, a first blood tubing in fluid communication with the inlet port, a second blood tubing in fluid communication with the outlet port, and a blood pump in operative engagement with at least one of the first blood tubing and the second blood tubing, wherein the diaphragm is configured such that at a pressure of −300 mmHg the diaphragm approaches but does not contact the interior bottom wall of the flow-through chamber.

The present invention can include any combination of these various features or embodiments above and/or below as set forth in sentences and/or paragraphs. Any combination of disclosed features herein is considered part of the present invention and no limitation is intended with respect to combinable features.

The entire contents of all references cited in this disclosure are incorporated herein in their entireties, by reference. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether such ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A pressure output device for sensing fluid pressure in a fluid processing system, the pressure sensing device comprising:
    a shell defining a shell interior; and
    a movable diaphragm disposed in the shell interior and separating the shell interior into a flow-through chamber defined by a lower portion of the shell and a first side of the diaphragm, and a pressure sensing chamber defined by an upper portion of the shell and a second side of the diaphragm, the second side being opposite the first side, the shell further defining a sensor port in fluid communication with the pressure sensing chamber, an inlet port in fluid communication with the flow-through chamber, and an outlet port in fluid communication with the flow-through chamber,
    wherein the inlet port and the outlet port define an inlet and an outlet, respectively, of a fluid flow path through the flow-through chamber, and the flow-through chamber has an interior wall and comprises a boss along the interior wall, which prevents the diaphragm from occluding flow through the fluid flow path.

2. The pressure output device of claim 1, wherein the inlet port has an axial center, the outlet port has an axial center, the axial center of the inlet port is substantially or completely aligned with the axial center of the outlet port, the boss protrudes from the interior wall and extends into the fluid flow path, and the boss includes at least one feature that intersects with a line that is co-axial with one or both of the axial centers.

3. The pressure output device of claim 1, wherein the fluid processing system is a hemodialysis machine, the fluid path is a blood path, and the boss comprises a diamond-shaped cross-section configured to minimize the potential for hemolysis due to occlusion of blood flow.

4. The pressure output device of claim 1, wherein the boss comprises a mid-section, a first end adjacent the inlet port, and a second end adjacent the outlet port, and the boss has a thickness that increases in a direction from the first end toward the mid-section and a thickness that increases in a direction from the second end toward the mid-section.

5. The pressure output devices of claim 4, wherein the boss has a width that increases in a direction from the first end toward the mid-section and a width that increases in a direction from the second end toward the mid-section.

6. A system comprising the pressure output device of claim 1, a pressure monitor, and a monitor line that forms a fluid communication between the sensor port and the pressure monitor.

7. A system comprising the pressure output device of claim 1, a first blood tubing in fluid communication with the inlet port, a second blood tubing in fluid communication with the outlet port, and a blood pump in operative engagement with at least one of the first blood tubing and the second blood tubing.

8. The pressure output device of claim 1, wherein the shell comprises a shell top and a shell bottom, the movable diaphragm comprises an outer periphery, and the outer periphery is sandwiched between the shell top and the shell bottom.

9. The pressure output device of claim 8, wherein the outer periphery of the movable diaphragm includes a groove, and at least one of the shell top and the shell bottom includes an outer peripheral shell rim configured to fit into the groove and engage the outer periphery of the movable diaphragm.

10. The pressure output device of claim 9, wherein the shell top and the shell bottom are bonded together, the movable diaphragm is positioned between the shell top and the shell bottom, and the outer peripheral rim is seated in the groove of the movable diaphragm.

11. The pressure output device of claim 9, wherein the groove is formed on a first side of the movable diaphragm, the outer periphery of the movable diaphragm comprises a rim along a second side of the movable diaphragm opposite the first side, the shell top comprises the outer peripheral shell rim, and the shell bottom comprises an outer peripheral groove configured to accommodate and engage the rim of the movable diaphragm.

12. The pressure output device of claim 1, wherein the diaphragm comprises a peripheral hinge and one or more hinge interruptions that form one or more respective discontinuances along the peripheral hinge.

13. The pressure output device of claim 1, wherein the lower portion of the shell comprises a shell interior wall, the interior wall of the flow-through chamber includes the shell interior wall, and the boss is arranged along the shell interior wall and spaced away from the first side of the diaphragm.

14. A pressure output device for sensing fluid pressure in a fluid processing system, the pressure sensing device comprising:
a shell defining a shell interior; and
a movable diaphragm disposed in the shell interior and separating the shell interior into a flow-through chamber defined by a lower portion of the shell and a first side of the diaphragm, and a pressure sensing chamber defined by an upper portion of the shell and a second side of the diaphragm, the second side being opposite the first side, the shell further defining a sensor port in fluid communication with the pressure sensing chamber, an inlet port in fluid communication with the flow-through chamber, and an outlet port in fluid communication with the flow-through chamber, the inlet port and the outlet port being aligned with one another along a first line,
wherein the inlet port and the outlet port define an inlet and an outlet, respectively, of a fluid flow path through the flow-through chamber, the flow-through chamber comprises an interior shell wall having a mid-section that includes a smooth uninterrupted surface that is continuous from a first point on the interior shell wall at a first intersection with the diaphragm to a second point on the interior shell wall at a second intersection with the diaphragm, the first and second points are arranged along a line that is perpendicular to the first line, the inlet of the fluid flow path merges with the smooth uninterrupted surface of the interior shell wall at a first partial interior shell wall cut-out, the outlet of the fluid flow path merges with the smooth uninterrupted surface of the interior shell wall at a second partial interior shell wall cut-out, the fluid flow path includes the first partial interior shell wall cut-out, the interior shell wall mid-section, and the second partial interior shell wall cut-out, and the first and second interior shell wall cut-outs do not intersect with one another.

15. The pressure output device of claim 14, wherein the inlet port has an axial center, the outlet port has an axial center, and the axial center of the inlet port is substantially or completely aligned with the axial center of the outlet port.

16. The pressure output device of claim 14, wherein the fluid processing system is a hemodialysis machine, the fluid flow path is a blood flow path, and the fluid flow path is configured to minimize the potential for hemolysis due to occlusion of blood flow.

17. A system comprising the pressure output device of claim 14, a pressure monitor, and a monitor line that forms a fluid communication between the sensor port and the pressure monitor.

18. A system comprising the pressure output device of claim 14, a first blood tubing in fluid communication with the inlet port, a second blood tubing in fluid communication with the outlet port, and a blood pump in operative engagement with at least one of the first blood tubing and the second blood tubing.

19. The pressure output device of claim 14, wherein the shell comprises a shell top and a shell bottom, the movable diaphragm comprises an outer periphery, and the outer periphery is sandwiched between the shell top and the shell bottom.

20. The pressure output device of claim 14, wherein the outer periphery of the movable diaphragm includes a groove, and at least one of the shell top and the shell bottom includes an outer peripheral shell rim configured to fit into the groove and engage the outer periphery of the movable diaphragm.

21. The pressure output device of claim 20, wherein the shell top and the shell bottom are bonded together, the movable diaphragm is positioned between the shell top and the shell bottom, and the outer peripheral rim is seated in the groove of the movable diaphragm.

22. The pressure output device of claim 20, wherein the groove is formed on a first side of the movable diaphragm, the outer periphery of the movable diaphragm comprises a rim along a second side of the movable diaphragm opposite the first side, the shell top comprises the outer peripheral shell rim, and the shell bottom comprises an outer peripheral groove configured to accommodate and engage the rim of the movable diaphragm.

23. A pressure output device for sensing fluid pressure in a fluid processing system, the pressure sensing device comprising:
a shell defining a shell interior; and
a movable diaphragm disposed in the shell interior and separating the shell interior into a flow-through chamber defined by a lower portion of the shell and a first side of the diaphragm, and a pressure sensing chamber defined by an upper portion of the shell and a second side of the diaphragm, the second side being opposite the first side, the shell further defining an interior bottom wall of the flow-through chamber, a sensor port in fluid communication with the pressure sensing chamber, a bypass channel separated from the flow-through chamber and formed underneath the interior bottom wall, an inlet chamber port that forms a first fluid communication between the flow-through chamber and the bypass channel, and an outlet chamber port that forms a second fluid communication between the flow-through chamber and the bypass channel,
wherein the bypass channel comprises an inlet port adjacent the inlet chamber port and configured to connect to an incoming blood line, and an outlet port adjacent the outlet chamber port and configured to connect to an outgoing blood line, and the bypass channel provides a non-occluded blood flow path from the inlet port to the outlet port even if the diaphragm completely occludes blood flow through the flow-through chamber.

24. The pressure output device of claim 23, wherein the bypass channel has a first diameter at the inlet port and a second, smaller diameter, between the inlet chamber port and the outlet chamber port.

25. The pressure output device of claim 24, wherein the bypass channel has a third diameter at the outlet port, which is larger than the second diameter between the inlet chamber port and the outlet chamber port.

26. A system comprising the pressure output device of claim 23 and a hemodialysis machine, the hemodialysis machine comprising a pressure monitor, wherein the system further comprises a pressure monitor line that forms a fluid communication between the sensor port and the pressure monitor.

27. A system comprising the pressure output device of claim 23, a first blood tubing in fluid communication with the inlet port, a second blood tubing in fluid communication with the outlet port, and a blood pump in operative engagement with at least one of the first blood tubing and the second blood tubing, wherein the diaphragm is configured such that at a pressure of −300 mmHg the diaphragm approaches but does not contact the interior bottom wall of the flow-through chamber.

\* \* \* \* \*